(12) United States Patent
Nakamura et al.

(10) Patent No.: US 7,943,364 B2
(45) Date of Patent: May 17, 2011

(54) METHOD FOR PRODUCING L-GLUTAMINE AND L-GLUTAMINE PRODUCING BACTERIUM

(75) Inventors: Jun Nakamura, Kawasaki (JP); Kayo Akiyama, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1867 days.

(21) Appl. No.: 10/720,177

(22) Filed: Nov. 25, 2003

(65) Prior Publication Data

US 2004/0152175 A1 Aug. 5, 2004

(30) Foreign Application Priority Data

Nov. 26, 2002 (JP) .................................. 2002-342287

(51) Int. Cl.
| | |
|---|---|
| C12N 1/21 | (2006.01) |
| C07K 14/00 | (2006.01) |
| C07H 21/00 | (2006.01) |
| C12P 21/00 | (2006.01) |
| C12P 13/14 | (2006.01) |
| C12N 9/00 | (2006.01) |
| C12N 9/78 | (2006.01) |
| C12Q 1/34 | (2006.01) |

(52) U.S. Cl. .................. 435/252.32; 435/69.1; 435/110; 435/227; 435/183; 435/18; 536/23.2; 530/350

(58) Field of Classification Search ............. 435/252.32, 435/69.1, 110, 227, 183, 18; 536/23.2; 530/350
See application file for complete search history.

(56) References Cited

U.S. PATENT DOCUMENTS

| | | | |
|---|---|---|---|
| 5,766,925 | A | 6/1998 | Sugimoto et al. |
| 5,908,768 | A | 6/1999 | Ono et al. |
| 2003/0003550 | A1 | 1/2003 | Nakamura et al. ............ 435/110 |
| 2003/0040098 | A1 | 2/2003 | Matsushima et al. |
| 2003/0124646 | A1 | 7/2003 | Yuasa et al. |
| 2003/0175936 | A1 | 9/2003 | Tahara |
| 2005/0014236 | A1 | 1/2005 | Matsuzaki et al. |
| 2006/0228712 | A1 | 10/2006 | Nakagawa et al. |

FOREIGN PATENT DOCUMENTS

| | | | |
|---|---|---|---|
| EP | 0796912 | | 9/1997 |
| EP | 0841395 | | 5/1998 |
| EP | 1033407 | | 9/2000 |
| EP | 1077256 | | 2/2001 |
| EP | 1108790 | * | 6/2001 |
| EP | 1 229 121 | A | 8/2002 |
| JP | 2000-88 | | 1/2000 |
| JP | 2002-191370 | | 7/2002 |
| JP | 2002-300887 | | 10/2002 |
| JP | 2003-33183 | | 2/2003 |
| JP | 2003-235566 | | 8/2003 |
| WO | WO95/23864 | | 9/1995 |
| WO | WO 01/00843 | | 1/2001 |

OTHER PUBLICATIONS

Seffernick et al., J. Bacteriol. 183(8):2405-2410, 2001.*
Branden et al., Introduction to Protein Structure, Garland Publishing Inc., New York, p. 247, 1991.*
Witkowski et al., Biochemistry 38:11643-11650, 1999.*
Duran et al., Microbiology 141:2883-2889, 1995.*
Current Protocols in Molecular Biology, Hybridization Analysis of DNA Blots, pp. 2.10.8-2.10.11, 1993.*
Nakagawa et al., GenBank accession No. AX127151, 2001.*
Kanno S. et al., Corynebacterium glutamicum gltB and gltD genes for glutamine 2-oxoglutarate aminotransferase large and small subunits, complete cds., GenBank Accession No. AB024708, Mar. 13, 1999.
Nakagawa S., Complete genomic sequence of Corynebacterium glutamicum ATCC 13032, GenBank Accession No. AP005281, May 24, 2002; Pertinant pp. 1, 133, 282-283.
Jakoby M. et al., Isolation of the *Corynebacterium glutamicum glnA* gene encoding glutamine synthetase I, FEMS Microbiology Letters, 1997, p. 81-88, vol. 154.
Huser A. et al., Cloning sequence analysis, and expression of *ansB* from *Pseudomonas fluorescens*, encoding periplasmic glutaminase/asparaginase, FEMS Microbiology Letters, 1990, p. 327-335, vol. 178.
Beckers G. et al., Glutamate synthethase of *Corynebacterium glutamicum* is not essential for glutamate synthesis and is regulated by the nitrogen status, Microbiology, 2001, p. 2961-2970, vol. 147.
Oshima et al., Studies on L-Glutamic Acid Fermentation to L-Glutamine Fermentation, Amino Acids, 1963, p. 73-77, vol. 7 (Partial English translation is attached.).
Koibuchi et al., Molecular cloning and characterization of a gene encoding glutaminase from *Aspergillus oryzae*, Appl. Microbiol. Biotechnol., 2000, p. 59-68, vol. 54.
Calderon J. et al., Sequence and molecular analysis of the *Rhizobium etli glsA* gene, encoding a thermolabile glutaminase, Biochimica et Biophysica Acta, 1999, p. 451-456, vol. 1444.
Shapiro A. R. et al., Isolation, Characterization, and in Vitro Expression of a cDNA That Encodes the Kidney Isoenzyme of the Mitochondrial Glutaminase, The Journal of Biological Chemistry, 1991, p. 18792-18796, vol. 266, No. 28.
Hartman C. S., Glutaminase of *Escherichia coli*, The Journal of Biological Chemistry, 1968, p. 853-863, vol. 243, No. 5.
Shulz A.A. et al., Nitrogen and carbon regulation of glutamine synthetase and glutamate synthase in *Corynebacterium glutamicum* ATCC 13032, FEMS Microbiology Letters, 2001, p. 361-367, vol. 205.
Jakoby M. J. et al., Corynebacterium glutamicum glnA gene, EMBL, Accession No. Y13221.1, Aug. 22, 1997.
Pompejus M. et al., Sequence 98 from Patent WO0100843, EMBL, Accession No. AX063816.1, Jan. 22, 2001.

(Continued)

*Primary Examiner* — Delia M Ramirez
(74) *Attorney, Agent, or Firm* — Shelly Guest Cermak; Cermak Nakajima LLP

(57) ABSTRACT

L-glutamine is produced by culturing a coryneform bacterium having L-glutamine-producing ability and modified so that intracellular glutaminase activity is reduced, and preferably also modified so that intracellular glutamine synthetase activity is enhanced. The method of production includes culturing the bacterium in a medium, followed by accumulation of L-glutamine in the medium and collecting the L-glutamine from the medium.

10 Claims, 4 Drawing Sheetse

OTHER PUBLICATIONS

Patek et al., Promoters from *Corynebacterium glutamicum*: cloning, Molecular analysis and search for a consensus motif, Microbiology, 1996, vol. 142, No. 5, pp. 1297-1309.

European Search Report, Apr. 14, 2004, EPO.

Hartman C. S., Glutaminase of *Escherichia coli*, The Journal of Biological Chemistry, 1968, p. 864-869, vol. 243, No. 5.

Hartman C. S., Glutaminase of *Escherichia coli*, The Journal of Biological Chemistry, 1968, p. 870-878, vol. 243, No. 5.

National Center for Biotechnology Information, Nucleotide, NC_003450, [online], Oct. 1, 2002, [retrieved on Feb. 24, 2009], Retrieved from the Internet: http://www.ncbi.nlm.nih.gov/entrez/viewer.fcgi?23308765:OLD03:2353272.

Notice of Reason for Rejection from Japanese Patent App. No. 2003-395175 (Mar. 3, 2009), with English translation thereof.

Japan Agricultural and Horticultural Chemistry Society Journal, 1961, vol. 35, No. 3, pp. 275-279 with English translation of Abstract.

Nakanishi, T., "Roles of Ammonium and Chloride Ions in the Conversion of L-Glutamic Acid Fermentation to L-Glutamine and N-Acetyl-L-Glutamine Fermentation by *Corynebacterium glutamicum*," J. Ferment. Technol. 1978;56(3):179-188.

Nakanishi, T., "Enzymes Concerned in the Conversion of L-Glutamic Acid Fermentation to L-Glutamine and N-Acetyl-L-Glutamine Fermentation by *Corynebacterium glutamicum*," J. Ferment. Technol. 1978;56(6):573-585.

Notice of Final Decision of Rejection for Japanese Patent App. No. 2003-395175 (Jun. 9, 2009) with English translation thereof.

* cited by examiner

```
SEQUENCE LISTING

<160> NUMBER OF SEQ ID NOS: 20

<210> SEQ ID NO 1
<211> LENGTH: 2100
<212> TYPE: DNA
<213> ORGANISM: Brevibacterium  flavum
<220> FEATURE:
<221> NAME/KEY: CDS
<222> LOCATION: (674)..(1999)

<400> SEQUENCE: 1
cacaaaatcc ggcgaatcca ccgaaatcgt cttcatcttt ggcttgatca aatgcctcat      60
tcggcccggc tgcaccgtca cgcttcgaga aatagaaata gcgcttgtcg acgccacccc     120
actctcaacg gcagccgcca gcgcgtggca tcagcccagg atttattagg accggcgata     180
taggtaatgg agtggcaccc ctgatccacc aaatgcacca cagccttcgc cgtaccgtcg     240
tagttatcca ccatcacgct gggaatacct tgcacttcac ggctcattaa tacagtggga     300
atttcccgcg cgactttgtg gatctcacca gaatccatcc ttgaagcagc gagcaataag     360
ccatcggcgt gggggacgat cttgtccagc acctccctgg acttaatcgc cgactcccgg     420
gcgtcgacaa gcgcaaccgt atagccctga gtgcttgcgg catgctgcgc gccctggaaa     480
atttccaaga agaagggatt cgatgcatcg gtggcaacca tagcgatgat accggtgttt     540
tggcgctgaa aagcctgagt ttccacacgc gttgcggatt ttctccgcag tggaaaaact     600
cactcgccca ggctgcgaaa acgcccgcga cacagtggaa ggggagacgc cagcgacttt     660
tgcgacatca taa atg gtg gct ttt gag tcg ctg tgg ccc cag aat ctg       709
               Met Val Ala Phe Glu Ser Leu Trp Pro Gln Asn Leu
                 1               5                  10 tca tgc aca aga gta tat agc gca aaa gaa atc act agt ctt gat tct     757
Ser Cys Thr Arg Val Tyr Ser Ala Lys Glu Ile Thr Ser Leu Asp Ser
       15                  20                  25
```

```
atg ttg acg atg ccg ata ccc gag tac ctg cac gaa att tta gat gat     805
Met Leu Thr Met Pro Ile Pro Glu Tyr Leu His Glu Ile Leu Asp Asp
    30              35                  40 gtc cgc gac acc acc tcc ggc gag ttg gcc gat tac atc ccg gaa cta     853
Val Arg Asp Thr Thr Ser Gly Glu Leu Ala Asp Tyr Ile Pro Glu Leu
45              50                  55                  60 aaa tct gcc gac cca aac ccg ctg gca gta gcc ctg tgc acc gtt aac     901
Lys Ser Ala Asp Pro Asn Pro Leu Ala Val Ala Leu Cys Thr Val Asn
                65                  70                  75 gga cac atc tac agc gca ggc gat gac gac atc gaa ttc acc atg caa     949
Gly His Ile Tyr Ser Ala Gly Asp Asp Asp Ile Glu Phe Thr Met Gln
            80                  85                  90 agt att tcc aag ccc ttt gcc tac gca ctc gca ctc caa gaa tgc ggc     997
Ser Ile Ser Lys Pro Phe Ala Tyr Ala Leu Ala Leu Gln Glu Cys Gly
        95                  100                 105 ttt gat gag gtc tct gca tcc gtg gcc ttg gaa ccc tcc ggt gag gcc    1045
Phe Asp Glu Val Ser Ala Ser Val Ala Leu Glu Pro Ser Gly Glu Ala
    110                 115                 120 ttc aac gaa ctt tcc ctc gac ggc gaa aac cgc ccc atg aac ccc atg    1093
Phe Asn Glu Leu Ser Leu Asp Gly Glu Asn Arg Pro Met Asn Pro Met
125                 130                 135                 140 atc aac gcc ggc gcg atc gcc atc aac cag ctg atc aac ggc tcc gac    1141
Ile Asn Ala Gly Ala Ile Ala Ile Asn Gln Leu Ile Asn Gly Ser Asp
                145                 150                 155 tcc acc gtg gaa gac cga gtg gaa aaa atc cga cac tac ttc tct gaa    1189
Ser Thr Val Glu Asp Arg Val Glu Lys Ile Arg His Tyr Phe Ser Glu
            160                 165                 170 ctt gct gga cgc gaa ctc acc atc gac cgc gtg ctt gcc gaa tcc gaa    1237
Leu Ala Gly Arg Glu Leu Thr Ile Asp Arg Val Leu Ala Glu Ser Glu
        175                 180                 185 ctc gcc ggc gcc gac cgc aac ctc tcc atc gcc cac atg ctg cgc aac    1285
Leu Ala Gly Ala Asp Arg Asn Leu Ser Ile Ala His Met Leu Arg Asn
    190                 195                 200 tat ggc gtc atc gaa gac gaa gcc cac gac gcc gtc ctc agc tac acg    1333
Tyr Gly Val Ile Glu Asp Glu Ala His Asp Ala Val Leu Ser Tyr Thr
205                 210                 215                 220 ctg caa tgt gcc atc aaa gta acc acg cgc gac ctc gca gtc atg acc    1381
Leu Gln Cys Ala Ile Lys Val Thr Thr Arg Asp Leu Ala Val Met Thr
                225                 230                 235 gcc acg ctc gcc gcc ggc ggc acg cac cca att acc ggc aag aag ctt    1429
Ala Thr Leu Ala Ala Gly Gly Thr His Pro Ile Thr Gly Lys Lys Leu
            240                 245                 250 ctc gac gcc cgc gtc tgc cgc ctc acc ctc tcc gtc atg gct tca gca    1477
Leu Asp Ala Arg Val Cys Arg Leu Thr Leu Ser Val Met Ala Ser Ala
        255                 260                 265 ggc atg tac gac gag gca ggg cag tgg ctc tcc acc gta ggc atc ccc    1525
Gly Met Tyr Asp Glu Ala Gly Gln Trp Leu Ser Thr Val Gly Ile Pro
    270                 275                 280 gcg aaa tca gga gtc gcc ggc gga ctc atc ggc att ctg cca ggt cag    1573
Ala Lys Ser Gly Val Ala Gly Gly Leu Ile Gly Ile Leu Pro Gly Gln
285                 290                 295                 300 ctg gga atc gcc aca ttt tcc cca cgc ctg aac ccc aaa ggc aac agc    1621
Leu Gly Ile Ala Thr Phe Ser Pro Arg Leu Asn Pro Lys Gly Asn Ser
                305                 310                 315 gtg cgc ggc gta aaa ata ttc aaa cag ctt tcc gac gac atg ggc ctc    1669
Val Arg Gly Val Lys Ile Phe Lys Gln Leu Ser Asp Asp Met Gly Leu
            320                 325                 330 cac ctt atg tcc acc gag cag gta tcc ggc cac gca gta cga tcc att    1717
His Leu Met Ser Thr Glu Gln Val Ser Gly His Ala Val Arg Ser Ile
        335                 340                 345
```

-continued

```
acg cgg gac ggc gac acc acc ttc atc caa atg cag ggc gcc atg aac    1765
Thr Arg Asp Gly Asp Thr Thr Phe Ile Gln Met Gln Gly Ala Met Asn
350                 355                 360 ttc tca gcc agc gaa agc ttc ctc cac gcc atc gtg gaa cac aac ttt    1813
Phe Ser Ala Ser Glu Ser Phe Leu His Ala Ile Val Glu His Asn Phe
365                 370                 375                 380 gaa ggc acc gaa gtt gtt ctt gat ctc acc cga gta ctt agc ttc cac    1861
Glu Gly Thr Glu Val Val Leu Asp Leu Thr Arg Val Leu Ser Phe His
                385                 390                 395 ccc gta gcc atc cgc atg atc aaa gaa ggc ctc aaa cgc atc cgc gac    1909
Pro Val Ala Ile Arg Met Ile Lys Glu Gly Leu Lys Arg Ile Arg Asp
            400                 405                 410 gca ggc ttt gag gtg ttc atc ctc gac cca gat gac gta ctg ccc gat    1957
Ala Gly Phe Glu Val Phe Ile Leu Asp Pro Asp Asp Val Leu Pro Asp
        415                 420                 425 ttc atg ttt tcc gac ggc acc atc tgc aaa gaa cga gtg tga            1999
Phe Met Phe Ser Asp Gly Thr Ile Cys Lys Glu Arg Val
    430                 435                 440 ccggtagctt tatggtctga acaattcgaa ggagattaat cggtgaaaaa gaagcttatg   2059
ttgcctttga ttgttgcagc tttgggatta agtgcctgca g                      2100

<210> SEQ ID NO 2
<211> LENGTH: 441
<212> TYPE: PRT
<213> ORGANISM: Brevibacterium flavum

<400> SEQUENCE: 2

Met Val Ala Phe Glu Ser Leu Trp Pro Gln Asn Leu Ser Cys Thr Arg
 1               5                  10                  15

Val Tyr Ser Ala Lys Glu Ile Thr Ser Leu Asp Ser Met Leu Thr Met
            20                  25                  30

Pro Ile Pro Glu Tyr Leu His Glu Ile Leu Asp Asp Val Arg Asp Thr
        35                  40                  45

Thr Ser Gly Glu Leu Ala Asp Tyr Ile Pro Glu Leu Lys Ser Ala Asp
    50                  55                  60

Pro Asn Pro Leu Ala Val Ala Leu Cys Thr Val Asn Gly His Ile Tyr
65                  70                  75                  80

Ser Ala Gly Asp Asp Asp Ile Glu Phe Thr Met Gln Ser Ile Ser Lys
                85                  90                  95

Pro Phe Ala Tyr Ala Leu Ala Leu Gln Glu Cys Gly Phe Asp Glu Val
            100                 105                 110

Ser Ala Ser Val Ala Leu Glu Pro Ser Gly Glu Ala Phe Asn Glu Leu
        115                 120                 125

Ser Leu Asp Gly Glu Asn Arg Pro Met Asn Pro Met Ile Asn Ala Gly
    130                 135                 140

Ala Ile Ala Ile Asn Gln Leu Ile Asn Gly Ser Asp Ser Thr Val Glu
145                 150                 155                 160

Asp Arg Val Glu Lys Ile Arg His Tyr Phe Ser Glu Leu Ala Gly Arg
                165                 170                 175

Glu Leu Thr Ile Asp Arg Val Leu Ala Glu Ser Glu Leu Ala Gly Ala
            180                 185                 190

Asp Arg Asn Leu Ser Ile Ala His Met Leu Arg Asn Tyr Gly Val Ile
        195                 200                 205

Glu Asp Glu Ala His Asp Ala Val Leu Ser Tyr Thr Leu Gln Cys Ala
    210                 215                 220

Ile Lys Val Thr Thr Arg Asp Leu Ala Val Met Thr Ala Thr Leu Ala
225                 230                 235                 240
```

```
Ala Gly Gly Thr His Pro Ile Thr Gly Lys Lys Leu Leu Asp Ala Arg
            245                 250                 255
Val Cys Arg Leu Thr Leu Ser Val Met Ala Ser Ala Gly Met Tyr Asp
            260                 265                 270
Glu Ala Gly Gln Trp Leu Ser Thr Val Gly Ile Pro Ala Lys Ser Gly
            275                 280                 285
Val Ala Gly Gly Leu Ile Gly Ile Leu Pro Gly Gln Leu Gly Ile Ala
        290                 295                 300
Thr Phe Ser Pro Arg Leu Asn Pro Lys Gly Asn Ser Val Arg Gly Val
305                 310                 315                 320
Lys Ile Phe Lys Gln Leu Ser Asp Asp Met Gly Leu His Leu Met Ser
                325                 330                 335
Thr Glu Gln Val Ser Gly His Ala Val Arg Ser Ile Thr Arg Asp Gly
            340                 345                 350
Asp Thr Thr Phe Ile Gln Met Gln Gly Ala Met Asn Phe Ser Ala Ser
            355                 360                 365
Glu Ser Phe Leu His Ala Ile Val Glu His Asn Phe Glu Gly Thr Glu
        370                 375                 380
Val Val Leu Asp Leu Thr Arg Val Leu Ser Phe His Pro Val Ala Ile
385                 390                 395                 400
Arg Met Ile Lys Glu Gly Leu Lys Arg Ile Arg Asp Ala Gly Phe Glu
                405                 410                 415
Val Phe Ile Leu Asp Pro Asp Asp Val Leu Pro Asp Phe Met Phe Ser
            420                 425                 430
Asp Gly Thr Ile Cys Lys Glu Arg Val
            435                 440

<210> SEQ ID NO 3
<211> LENGTH: 2500
<212> TYPE: DNA
<213> ORGANISM: Brevibacterium flavum
<220> FEATURE:
<221> NAME/KEY: CDS
<222> LOCATION: (874)..(2307)

<400> SEQUENCE: 3
ctctgtgcgg ggacgaaaat ttgcaactct cgctttgtct agctagatca accccaacca     60
agcacgaagg gcgtcgatcc ccgcaaagat cggcgcccat aaatttcact caagacaaat    120
tacccgcgga taactgcagt tcccgttgcc ttgtcgtgga gcccacggcc gtcagcatcc    180
accatcacgg caggcagaat caaaatggtc agcagtggac gaaccagcgc acgccaccaa    240
cccacacgct cctctgcatc cacacgcgca aggcccatgc caaacacggc atgacctggg    300
gtgcgagcaa agatccatcc cgttagccaa cccaggatca cgaaaataat gagcgtggat    360
gtcgctacat cgcccagcac atccgtgaaa ttggacagca caatagcaat aacccaggaa    420
acaccccagt ccacgcagac cccgccgata cgacgagcca ctgaggacag agagccggcc    480
ccttcttgag gaagcccaa cttttcgcca ggccacctgc cgggcgcatc aggatcgtca    540
aaatcagctg gaatttcggg tccgtcaagc caacttctct tcggctttgc cattgttaca    600
atcaaatcca acatgtaga gggcggatac tgcagtcaaa aggcgttgcc tttagacgtc    660
gcaaagcgca atttcctacc tttaagatcc taatctgttg aggtcagcca caattttttca    720 gaaaagttttt gatagatcga caggtaatgc attatactga caacgtcgca aggactacat    780
ttgcagccaa gtctactact tgatcttcaa aggtcagcaa ttgtgaacaa agctacaaat    840
aaaccgttcc acccatgtca atgaggagtc acc gtg gcg ttt gaa acc ccg gaa    894
```

```
                      Val Ala Phe Glu Thr Pro Glu
                       1               5 gaa att gtc aag ttc atc aag gat gaa aac gtc gag ttc gtt gac gtt     942
Glu Ile Val Lys Phe Ile Lys Asp Glu Asn Val Glu Phe Val Asp Val
         10                  15                  20 cga ttc acc gac ctt ccc ggc acc gag cag cac ttc agc atc cca gct     990
Arg Phe Thr Asp Leu Pro Gly Thr Glu Gln His Phe Ser Ile Pro Ala
     25                  30                  35 gcc agc ttc gat gca gat aca gtc gaa gaa ggt ctc gca ttc gac gga    1038
Ala Ser Phe Asp Ala Asp Thr Val Glu Glu Gly Leu Ala Phe Asp Gly
 40              45                  50                      55 tcc tcg atc cgt ggc ttc acc acg atc gac gaa tct gac atg aat ctc    1086
Ser Ser Ile Arg Gly Phe Thr Thr Ile Asp Glu Ser Asp Met Asn Leu
                     60                  65                  70 ctg cca gac ctc gga acg gcc acc ctt gat cca ttc cgc aag gca aag    1134
Leu Pro Asp Leu Gly Thr Ala Thr Leu Asp Pro Phe Arg Lys Ala Lys
                 75                  80                  85 acc ctg aac gtt aag ttc ttc gtt cac gat cct ttc acc cgc gag gca    1182
Thr Leu Asn Val Lys Phe Phe Val His Asp Pro Phe Thr Arg Glu Ala
             90                  95                 100 ttc tcc cgc gac cca cgc aac gta gca cgc aag gca gag cag tac ctg    1230
Phe Ser Arg Asp Pro Arg Asn Val Ala Arg Lys Ala Glu Gln Tyr Leu
        105                 110                 115 gca tcc acc ggc att gca gac acc tgc aac ttc ggc gcc gag gct gag    1278
Ala Ser Thr Gly Ile Ala Asp Thr Cys Asn Phe Gly Ala Glu Ala Glu
120                 125                 130                 135 ttc tac ctc ttc gac tcc gtt cgc tac tcc acc gag atg aac tcc ggc    1326
Phe Tyr Leu Phe Asp Ser Val Arg Tyr Ser Thr Glu Met Asn Ser Gly
                140                 145                 150 ttc tac gaa gta gat acc gaa gaa ggc tgg tgg aac cgt ggc aag gaa    1374
Phe Tyr Glu Val Asp Thr Glu Glu Gly Trp Trp Asn Arg Gly Lys Glu
            155                 160                 165 acc aac ctc gac gga acc cca aac ctg ggc gca aag aac cgc gtc aag    1422
Thr Asn Leu Asp Gly Thr Pro Asn Leu Gly Ala Lys Asn Arg Val Lys
        170                 175                 180 ggt ggc tac ttc cca gta gca cca tac gac caa acc gtt gac gtg cgc    1470
Gly Gly Tyr Phe Pro Val Ala Pro Tyr Asp Gln Thr Val Asp Val Arg
185                 190                 195 gat gac atg gtt cgc aac ctc gca gct tcc ggc ttc gct ctt gag cgt    1518
Asp Asp Met Val Arg Asn Leu Ala Ala Ser Gly Phe Ala Leu Glu Arg
200                 205                 210                 215 ttc cac cac gaa gtc ggt ggc gga cag cag gaa atc aac tac cgc ttc    1566
Phe His His Glu Val Gly Gly Gly Gln Gln Glu Ile Asn Tyr Arg Phe
                220                 225                 230 aac acc atg ctc cac gcg gca gat gat atc cag acc ttc aag tac atc    1614
Asn Thr Met Leu His Ala Ala Asp Asp Ile Gln Thr Phe Lys Tyr Ile
            235                 240                 245 atc aag aac acc gct cgc ctc cac ggc aag gct gca acc ttc atg cct    1662
Ile Lys Asn Thr Ala Arg Leu His Gly Lys Ala Ala Thr Phe Met Pro
        250                 255                 260 aag cca ctg gct ggc gac aac ggt tcc ggc atg cac gct cac cag tcc    1710
Lys Pro Leu Ala Gly Asp Asn Gly Ser Gly Met His Ala His Gln Ser
265                 270                 275 ctc tgg aag gac ggc aag cca ctc ttc cac gat gag tcc ggc tac gca    1758
Leu Trp Lys Asp Gly Lys Pro Leu Phe His Asp Glu Ser Gly Tyr Ala
280                 285                 290                 295 ggc ctg tcc gac atc gcc cgc tac tac atc ggc ggc atc ctg cac cac    1806
Gly Leu Ser Asp Ile Ala Arg Tyr Tyr Ile Gly Gly Ile Leu His His
                300                 305                 310 gca ggc gct gtt ctg gcg ttc acc aac gca acc ctg aac tcc tac cac    1854
```

```
Ala Gly Ala Val Leu Ala Phe Thr Asn Ala Thr Leu Asn Ser Tyr His
            315                 320                 325 cgt ctg gtt cca ggc ttc gag gct cca atc aac ctg gtg tac tca cag   1902
Arg Leu Val Pro Gly Phe Glu Ala Pro Ile Asn Leu Val Tyr Ser Gln
        330                 335                 340 cgc aac cgt tcc gct gct gtc cgt atc cca atc acc gga tcc aac cca   1950
Arg Asn Arg Ser Ala Ala Val Arg Ile Pro Ile Thr Gly Ser Asn Pro
    345                 350                 355 aag gca aag cgc atc gaa ttc cgc gct cca gac cca tca ggc aac cca   1998
Lys Ala Lys Arg Ile Glu Phe Arg Ala Pro Asp Pro Ser Gly Asn Pro
360                 365                 370                 375 tac ctg ggc ttc gca gcg atg atg atg gcc ggc ctc gac ggc atc aag   2046
Tyr Leu Gly Phe Ala Ala Met Met Met Ala Gly Leu Asp Gly Ile Lys
                380                 385                 390 aac cgc atc gag cca cac gct cca gtg gac aag gac ctc tac gaa ctg   2094
Asn Arg Ile Glu Pro His Ala Pro Val Asp Lys Asp Leu Tyr Glu Leu
            395                 400                 405 cca cca gag gaa gct gca tcc att cca cag gca cca acc tcc ctg gaa   2142
Pro Pro Glu Glu Ala Ala Ser Ile Pro Gln Ala Pro Thr Ser Leu Glu
        410                 415                 420 gca tcc ctg aag gca ctg cag gaa gac acc gac ttc ctc acc gag tct   2190
Ala Ser Leu Lys Ala Leu Gln Glu Asp Thr Asp Phe Leu Thr Glu Ser
    425                 430                 435 gac gtc ttc acc gag gat ctc atc gag gcg tac atc cag tac aag tac   2238
Asp Val Phe Thr Glu Asp Leu Ile Glu Ala Tyr Ile Gln Tyr Lys Tyr
440                 445                 450                 455 gac aac gag atc tcc cca gtt cgc ctg cgc cca acc ccg cag gaa ttc   2286
Asp Asn Glu Ile Ser Pro Val Arg Leu Arg Pro Thr Pro Gln Glu Phe
                460                 465                 470 gaa ttg tac ttc gac tgc taa ttcacttagc tagccgatag cggaaacccc      2337
Glu Leu Tyr Phe Asp Cys
            475 ctgaaattct tcattgaatt tcaggggggtt tcttttttac attccaccta aaaggaaagc   2397 gccggatcct ccatcatggt ggatccggcg cttttatcta tttgttttttg ggctagatgc   2457 cgatcagttc agatgcaact acatcggaca gtgagacggt tcc                    2500

<210> SEQ ID NO 4
<211> LENGTH: 477
<212> TYPE: PRT
<213> ORGANISM: Brevibacterium flavum

<400> SEQUENCE: 4

Val Ala Phe Glu Thr Pro Glu Glu Ile Val Lys Phe Ile Lys Asp Glu
  1               5                  10                  15

Asn Val Glu Phe Val Asp Val Arg Phe Thr Asp Leu Pro Gly Thr Glu
             20                  25                  30

Gln His Phe Ser Ile Pro Ala Ala Ser Phe Asp Ala Asp Thr Val Glu
         35                  40                  45

Glu Gly Leu Ala Phe Asp Gly Ser Ser Ile Arg Gly Phe Thr Thr Ile
     50                  55                  60

Asp Glu Ser Asp Met Asn Leu Leu Pro Asp Leu Gly Thr Ala Thr Leu
 65                  70                  75                  80

Asp Pro Phe Arg Lys Ala Lys Thr Leu Asn Val Lys Phe Phe Val His
                 85                  90                  95

Asp Pro Phe Thr Arg Glu Ala Phe Ser Arg Asp Pro Arg Asn Val Ala
            100                 105                 110

Arg Lys Ala Glu Gln Tyr Leu Ala Ser Thr Gly Ile Ala Asp Thr Cys
        115                 120                 125
```

```
Asn Phe Gly Ala Glu Ala Glu Phe Tyr Leu Phe Asp Ser Val Arg Tyr
    130                 135                 140

Ser Thr Glu Met Asn Ser Gly Phe Tyr Glu Val Asp Thr Glu Glu Gly
145                 150                 155                 160

Trp Trp Asn Arg Gly Lys Glu Thr Asn Leu Asp Gly Thr Pro Asn Leu
                165                 170                 175

Gly Ala Lys Asn Arg Val Lys Gly Gly Tyr Phe Pro Val Ala Pro Tyr
            180                 185                 190

Asp Gln Thr Val Asp Val Arg Asp Met Val Arg Asn Leu Ala Ala
        195                 200                 205

Ser Gly Phe Ala Leu Glu Arg Phe His His Glu Val Gly Gly Gln
210                 215                 220

Gln Glu Ile Asn Tyr Arg Phe Asn Thr Met Leu His Ala Ala Asp Asp
225                 230                 235                 240

Ile Gln Thr Phe Lys Tyr Ile Ile Lys Asn Thr Ala Arg Leu His Gly
            245                 250                 255

Lys Ala Ala Thr Phe Met Pro Lys Pro Leu Ala Gly Asp Asn Gly Ser
            260                 265                 270

Gly Met His Ala His Gln Ser Leu Trp Lys Asp Gly Lys Pro Leu Phe
            275                 280                 285

His Asp Glu Ser Gly Tyr Ala Gly Leu Ser Asp Ile Ala Arg Tyr Tyr
290                 295                 300

Ile Gly Gly Ile Leu His His Ala Gly Ala Val Leu Ala Phe Thr Asn
305                 310                 315                 320

Ala Thr Leu Asn Ser Tyr His Arg Leu Val Pro Gly Phe Glu Ala Pro
                325                 330                 335

Ile Asn Leu Val Tyr Ser Gln Arg Asn Arg Ser Ala Ala Val Arg Ile
            340                 345                 350

Pro Ile Thr Gly Ser Asn Pro Lys Ala Lys Arg Ile Glu Phe Arg Ala
            355                 360                 365

Pro Asp Pro Ser Gly Asn Pro Tyr Leu Gly Phe Ala Ala Met Met Met
370                 375                 380

Ala Gly Leu Asp Gly Ile Lys Asn Arg Ile Glu Pro His Ala Pro Val
385                 390                 395                 400

Asp Lys Asp Leu Tyr Glu Leu Pro Pro Glu Glu Ala Ala Ser Ile Pro
                405                 410                 415

Gln Ala Pro Thr Ser Leu Glu Ala Ser Leu Lys Ala Leu Gln Glu Asp
            420                 425                 430

Thr Asp Phe Leu Thr Glu Ser Asp Val Phe Thr Glu Asp Leu Ile Glu
            435                 440                 445

Ala Tyr Ile Gln Tyr Lys Tyr Asp Asn Glu Ile Ser Pro Val Arg Leu
        450                 455                 460

Arg Pro Thr Pro Gln Glu Phe Glu Leu Tyr Phe Asp Cys
465                 470                 475

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 5
cacaaaatcc ggcgaatcca                                              20
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 6
ctgcaggcac ttaatcccaa                                               20

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 7
ccggcgagtt cggattcaaa gccgcattct tgg                                33

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 8
ctccaagaat gcggctttga atccgaactc gccgg                              35

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 9
ctcccgggcg tcgacaagcg caacc                                         25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 10
gccccggggt ggaagctaag tactc                                         25

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 11
cgcccgggtt ccactgagcg tcagac                                        26

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 12

```
gatcccgggg atcccgtcgt tttacaac                                      28

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 13
agatcggcgc ccataaattt c                                             21

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 14
cccccccggg gtaactgcag ttcccgttgc                                    30

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 15
gtttggggtt ccgtcgaggt tggt                                          24

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 16
cccccggggt tccaccagcc ttcttc                                        26

<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 17
cagaaaagtt gccatagatc gacaggtaat gctataatct gacaacgtcg c            51

<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 18
gcgacgttgt cagattatag cattacctgt cgatctatgg caacttttct g            51

<210> SEQ ID NO 19
<211> LENGTH: 29
<212> TYPE: DNA
<213> ORGANISM: Artificial Sequence
```

```
<220> FEATURE:
<223> OTHER INFORMATION: Description of Artificial Sequence: primer

<400> SEQUENCE: 19
ggggtcgacg gatcgacagg taatgcatt                                              29

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 20
ggggtcgacg gatccaccat gatggagga                                              29
```

US 7,943,364 B2

METHOD FOR PRODUCING L-GLUTAMINE AND L-GLUTAMINE PRODUCING BACTERIUM

BACKGROUND OF THE INVENTION

1. Field of the Invention

The present invention relates to an L-glutamine-producing bacterium belonging to coryneform bacteria, and which is useful for production of L-glutamine. The present invention also relates to a method for producing L-glutamine. L-glutamine is an industrially useful amino acid as an ingredient in seasonings, liver function promoting agents, amino acid infusions, comprehensive amino acid pharmaceuticals and so forth.

2. Brief Description of the Related Art

Various techniques for increasing L-amino acid production using recombinant DNA techniques have been disclosed. For example, techniques for enhancing activities of enzymes involved in L-amino acid biosyntheses (WO96/40934), or techniques for reducing activities of enzymes involved in degradation of L-amino acids (WO/96/17930), and so fort, are known. A method for producing L-glutamine using a coryneform bacterium having enhanced glutamine synthetase activity has been disclosed (US Pat App Pub No. 2003/0003550). Furthermore, genes encoding glutamine synthetase (Genbank Accession No. Y13221) and glutamine 2-oxoglutarate aminotranferase (Genbank Accession No. AB024708) have been reported (FEMS Microbiol. Le (1997) 154(1) 81-88, Microbiology (2001) 147, 2961-2970), and are known to be involved in glutamine biosynthesis and degradation of coryneform bacteria.

Besides the aforementioned genes, existence of an enzyme involved in degradation of L-glutamine in coryneform bacteria has been suggested (Amino Acids, 7:73-77 (1963)). However, this enzyme is inhibited by ammonium ions and low pH, and thus barely functions in glutamine fermentation in the presence of the required ammonium ions.

Glutamine (glutamine amidohydrolase) is known as an enzyme that degrades L-glutamine by hydrolysis. Genes encoding glutaminase have been reported for *Pseudomonas* bacteria (FEMS Microbiol. lett., 178 (2), 327-335 (1999)), *Aspergillus oryzae* (Appl. Microbiol. Biotechnol., 54, 59-68 (2000), EP 1 077 256 A1), *Rhizobium etli* (Biochim. Biophys. Acta, 1444 (3): 451-6, 1999), rat (J. Biol. Chem., 266(28): 18792-18796(1991)), amongothers. Furthermore, existence of glutaminase activity in *Escherichia coli* has been reported (J. Biol. Chem., 243 (5) 853-878 (1968)). However, a glutaminase gene derived from coryneform bacteria has not been identified, and any effect mutation of such a gene will have on glutamine production is not known.

A method for enhancing gene expression by modifying a promoter sequence of the desired gene is known (Japanese Patent Laid-open (Kokai) No. 2000-818935). Furthermore, a gene encoding glutamine synthetase (hereiner, "glnA") from coryneform bacteria is known (FEMS Microbiology Letters, 154, 81-88, 1997). Moreover, the transcription initiation site of the gene including the promoter region has been identified (FEMS Microbiology Letters, 205, 361-367, 2001). However, enhancing the expression of the glutamine synthetase gene by modifying a promoter sequence has not been previously described.

Methods of improving microorganisms by breeding have frequently been used in fermentation production of L-amino acids. That is, since the yield of L-amino acids produced from wild-type microorganisms is often extremely low, methods of imparting auxotrophic or analogue resistance by mutation, or imparting mutations designed to improve metabolic regulation, or a combination of these are known. Although L-glutamine can be obtained by these known methods, there is clearly a need in the art to improve fermentation yields so that production of L-glutamine can be accomplished efficiently and at a low cost.

SUMMARY OF THE INVENTION

The inventors of the present invention assiduously studied in order to achieve the present invention. The present invention describes a novel gene present in a coryneform bacteria, as well as methods for improved production of L-glutamine using recombinant techniques. Initially, a gene was identified encoding glutaminase, and at the same time, it was discovered that L-glutamine-producing ability was far superior in a strain with reduced glutaminase activity than in a strain where glutaminase activity was similar to that of a wild-type strain. Furthermore, it was discovered that the L-glutamine-producing ability could be further improved by reducing glutaminase activity while simultaneously enhancing glutamine synthetase activity.

An object of the present invention is to improve L-glutamine-producing ability of a coryneform bacterium by reducing L-glutamine degradation ability of the coryneform bacterium, and thereby provide a method for producing L-glutamine by utilizing a bacterial strain having such a characteristic.

It is a further object of the present invention to provide a coryneform bacterium having L-glutamine producing ability and modified so that intracellular glutaminase activity is reduced.

It is a further object of the present invention to provide the bacterium as stated above, wherein the intracellular glutaminase activity is reduced by disrupting a glutaminase gene on a chromosome.

It is even a further object of the present invention to provide the bacterium as stated above, wherein the glutaminase activity is 0.1 U/mg of cellular protein or less.

It is even a further object of the present invention to provide the bacterium as stated above, wherein the glutaminase activity is similar to or less than glutamine synthetase activity when measured as activity per unit weight of cellular proteins.

It is even a further object of the present invention to provide the bacterium as stated above, which is further modified so that intracellular glutamine synthetase activity is enhanced.

It is even a further object of the present invention to provide the bacterium as stated above, wherein the glutamine synthetase activity is enhanced by increasing the expression of a glutamine synthetase gene.

It is even a further object of the present invention to provide the bacterium as stated above, wherein enhancing the expression of a glutamine synthetase gene is attained by increasing the copy number of the gene encoding glutamine synthetase, or modifying an expression regulatory sequence of the gene encoding glutamine synthetase, so that expression of the gene in the bacterium is enhanced.

It is even a further object of the present invention to provide a method for producing L-glutamine, comprising the steps of culturing a bacterium as stated above in a medium to produce L-glutamine in the medium and collecting the L-glutamine from the medium.

It is even a further object of the present invention to provide a glutamine synthetase gene of a coryneform bacterium, wherein the sequence of −35 region of the gene is replaced with TFGCCA, and the sequence of −10 region of the gene is replaced with TATAAT.

According to the present invention, L-glutamine-producing ability of coryneform bacteria can be improved, resulting in greater yields of L-glutamine produced efficiency and at low cost.

DETAILED DESCRIPTION OF TEE PREFERRED EMBODIMENTS

Coryneform Bacterium of the Present Invention

Figure 1:
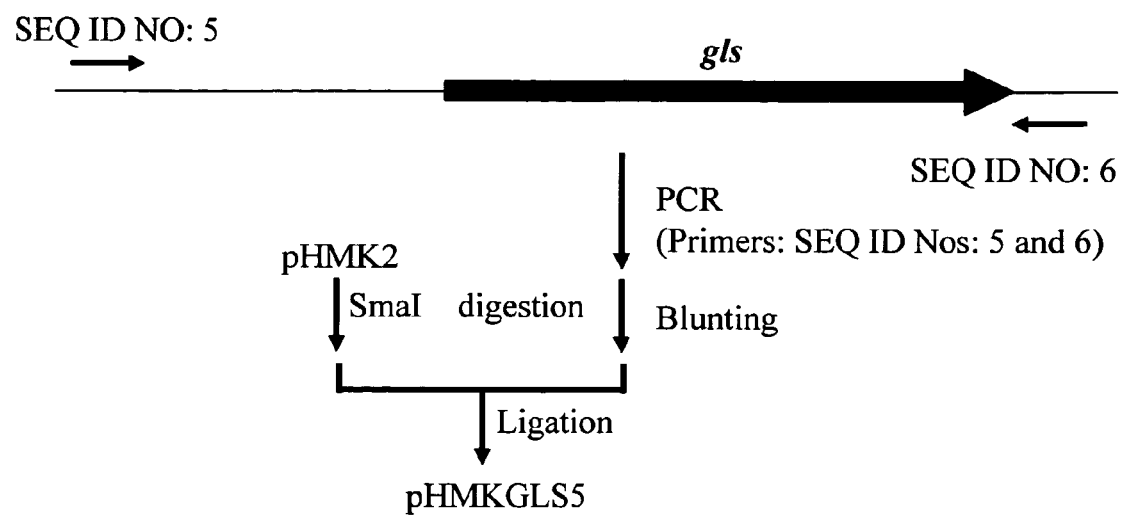
FIG. 1 shows scheme for construction of plasmid pHMKGLS5 containing a glutaminase gene.

In the present invention, coryneform bacteria include, but are not limited to those bacteria classified in the genus *Brevibacterium*, as well as those classified in the genus *Corynebacterium* (Int J. Syst Bacteriol., 41, 255(1981)), which are closely related. Examples of such coryneform bacteria include but are not limited to *Corynebacterium acetoacidophilum*, *Corynebacterium acetoglutamicum*, *Corynebacterium alkanolyticum*, *Corynebacterium callunae*, *Corynebacterium glutamicum*, *Corynebacterium lilium*, *Corynebacterium melassecola*, *Corynebacterium thermoaminogenes*, *Corynebacterium herculis*, *Brevibacterium divaricatum*, *Brevibacterium flavum*, *Brevibacterium immariophilum*, *Brevibacterium lactofermentum*, *Brevibacterium roseum*, *Brevibacterium saccharolyticum*, *Brevibacterium thiogenitalis*, *Corynebacterium ammoniagenes*, *Brevibacterium album*, *Brevibacterium cerium*, and *Microbacterium ammoniaphilum*.

Specifically, the following stains are encompassed: *Corynebacterium acetoacidophilum* ATCC 13870, *Corynebacterium acetoglutamicum* ATCC 15806, *Corynebacterium alkanolyticum* ATCC 21511, *Corynebacterium callunae* ATCC 15991, *Corynebacterium glutamicum* ATCC 13020, 13032, 13060, *Corynebacterium lilium* ATCC 15990, *Corynebacterium melassecola* ATCC 17965, *Corynebacterium thermoaminogenes* AJ12340 (FERM BP-1539), *Corynebacterium herculis* ATCC 13868, *Brevibacterium divaricatum* ATCC 14020, *Brevibacterium flavum* ATCC 13826, ATCC 14067, AJ12418 (FERM BP-2205), *Brevibacterium immariophilum* ATCC 14068, *Brevibacterium lactofermentum* ATCC 13869, *Brevibacterium roseum* ATCC 13825, *Brevibacterium saccharolyticum* ATCC 14066, *Brevibacterium thiogenitalis* ATCC 19240, *Brevibacterium ammoniagenes* ATCC 6871, ATCC 6872, *Brevibacterium album* ATCC 15111, *Brevibacterium cerium* ATCC 15112, and *Microbacterium ammoniaphilum* ATCC 15354.

These strains can be obtained from, for example, the American Type Culture Collection. Each strain is assigned its accession number, and one can request a desired strain by its accession number. The accession number for each strain is indicated on the catalog of the American Type Culture Collection. The AJ12340 strain was deposited on Oct. 27, 1987 at National Institute of Bioscience and Human-Technology, Agency of Industrial Science and Technology, Ministry of International Trade and Industry (currently, the independent administrative corporation, National Institute of Advanced Industrial Science and Technology, International Patent Organism Depositary (Tsukuba Central 6, 1-1, Higashi 1-Chrome, Tsukuba-shi, Ibaraki-ken, Japan, postal code: 305-5466)) as an international deposit under the provisions of the Budapest Treaty, receiving an accession number of FERM BP-1539. The AJ12418 strain was deposited on Jan. 5, 1989 at National Institute of Bioscience and Human-Technology, Agency of Industrial Science and Technology, Ministry of International Trade and Industry as an international deposit under the provisions of the Budapest Treaty, receiving an accession number of FERM BP-2205.

In the present invention, "L-glutamine-producing ability" means an ability of the coryneform bacterium of the present invention to accumulate L-glutamine in a medium when the bacterium is cultured in the medium. This L-glutamine-producing ability may be a property of a wild-type strain of coryneform bacteria or may be a property imparted or enhanced by breeding.

The method of imparting 6-diazo-5-oxo-norleucine resistance (Japanese Patent Laid-open No. 3-232497), the method of imparting purine analogue resistance and/or methionine sulfoxide resistance (Japanese Patent Laid-pen No. 61-202694), the method of imparting α-ketomalonic acid resistance (Japanese Patent Laid-pen No. 56-151495), the method of imparting resistance to a peptide containing glutamic acid (Japanese Patent Laid-open No. 2-186994) and so forth can be used to impart or enhance the L-glutamine-producing ability by breeding. Specific examples of coryneform bacteria having L-glutamine-producing ability include, but are not limited to: *Brevibacterium flavum* AJ11573 (FERM P-5492, refer to Japanese Patent Laid-open No. 56-151495); *Brevibacterium flavum* AJ 12210 (FERM P-8123, refer to Japanese Patent Laid-open No. 61-202694); *Brevibacterium flavum* AJ12212 (FERM P-8123, refer to Japanese Patent Laid-open No. 61-202694); *Brevibacterium flavum* AJ12418 (FERM-BP2205, refer to Japanese Patent Laid-open No. 2-186994); *Brevibacterium flavum* DH18 (FERM P-11116, refer to Japanese Patent Laid-open No. 3-232497); *Corynebacterium melassecola* DH344 (FERM P-11117, refer to Japanese Patent Laid-open No. 3-232497); *Corynebacterium glutamicum* AJ1574 (FERM P-5493, refer to Japanese Patent Laid-open No. 56-151495).

In addition, the coryneform bacterium of the present invention may be modified so that the intracellular glutaminase activity is reduced. The "glutaminase activity" (hereinafter, "GLS activity") means an enzymatic activity of converting L-glut mine to L-glutamic acid The GLS activity can be measured for example, by the following method, among others known in the art.

A crude enzyme solution of coryneform bacterium is added to a solution containing 100 mM Tris-HCl (pH 8.0) and 75 mM L-glutamine, and a reaction is allowed at 30° C. for 30 minutes or 60 minutes. Then, SDS is added to the reaction mixture at a final concentration of 0.5% to terminate the reaction, and the resultant L-glutamic acid is quantified. In the present invention, glutaminase activity producing 1 μmol of glutamic acid per minute in the aforementioned reaction system is defined as 1 U. The amount of protein in the crude enzyme solution can be measured by a known method, for example, by using Protein Assay (Bio-Rad) with a bovine serum albumin standard Hereinafter, the GLS activity per 1 mg of protein is indicated with the unit "U/mg".

The aforementioned crude enzyme solution can be prepared, for example, as follows. First, to prepare cells, 20 ml of a medium containing 30 g of glucose, 1.5 g of $KH_2PO_4$, 0.4 g of MgSO$_4$.7H$_2$O, 0.01 g of FeSO$_4$.7H$_2$O, 100 μg of VB$_1$HCl, 3 μg of biotin, 200 mg of soybean hydrolysates, 1.5 g of urea and 0.02 ml of antifoam agent GD-113 in 1 L of pure water (adjusted to pH 6.8 with NaOH) is introduced into a 500 ml Sakaguchi flask. After sterilization of the medium by autoclave at 115° C. for 10 minutes, the cells of the strain are inoculated into the medium and cultured at 31.5° C. with shaking at 115 rpm. The culture is finished before the sugar is completely consumed, and the culture broth is instantly cooled. The cells are separated from the culture broth by centrifugation with refrigeration, washed with 100 mM Tris-HCl (pH 8.0) and disrupted by sonication. The undisrupted cells are removed by centrifugation at 15000 g for 15 minute to prepare a crude enzyme solution. The crude enzyme solution is placed on ice until use.

According to the aforementioned method, GLS activities of known L-glutamine-producing bacteria were measured and the results are shown in Table 8.

The expression "modified so that intracellular glutaminase activity is reduced" means that the bacterium has been modified so that the GLS activity per cell becomes lower than that of a wild-type or non-modified strain of coryneform bacterium. Examples include when the number of GLS (glutaminase) molecules per cell decreases, or when GLS activity per GLS molecule decreases and so forth The "reduction" also includes complete disappearance of activity. A stain or non-modified strain of coryneform bacterium may be compared to, for example, the *Brevibacterium flavum* ATCC 14067. As a result of reduction of GLS activity, the amount of L-glutamine accumulation in a medium increases, and the by-product L-glutamic acid in a medium decreases.

It is sufficient that the coryneform bacterium of the present invention has reduced GLS activity compared with a wild-type strain or non-modified strain. Preferably, the GLS activity as measured in the aforementioned measurement system may be reduced to a level of 0.1 U/mg or less, preferably 0.02 U/mg or less, more preferably 0.01 U/mg or less. However, the present invention is not limited to the activity of 0.01 U/mg or less.

Although the gene encoding GLS of coryneform bacteria had not been previously identified, the present invention encompasses a gene which was isolated by the inventors from *Brevibacterium flavum*. They searched genes of *Corynebacterium glutamicumr* for a homologous gene to the known GLS gene of *Rhizobium* bacterium (Biochim BiophysActa, 1444(3): 451-6, Mar. 19, 1999) using the published genome sequence of *Corynebacterium glutamicum* and they found a gene which was estimated to encode GLS. Based on the sequence of the putative GLS gene of *Corynebacterium glutamicum* they isolated GLS gene from *Brevibacterium flavum*, and which is homologous with the GLS gene of a *Rhizobium* bacterium (Biochim Biophys Acta, 1444(3): 451-6, Mar. 19, 1999). The gls gene can be obtained by PCR (see White, T. J. et al., Trends Genet, 5, 185 (1989)) using primers based on that nucleotide sequence, for example, the primers shown in SEQ ID NOS: 5 and 6, and chromosomal DNA of coryneform bacterium as a template. Genes encoding GLS from other microorganisms can also be similarly obtained. The gls gene of the *Brevibacterium flavum* ATCC 14067 strain obtained as described above is shown in SEQ ID NO: 1, and the amino acid sequence encoded thereby is shown in SEQ ID NO: 2.

The chromosomal DNA can be prepared from a bacterium serving as a DNA donor by, for example, the method of Saito and Miura (see H. Saito and K. Miura, Biochem. Biophys. Acta, 72, 619 (1963), Text for Bioengineering Experiments, Edited by the Society for Bioscience and Bioengineering, Japan, pp. 97-98, Baifukan, 1992) and the like.

Methods for reducing the GLS activity of coryneform bacteria include, but are not limited to, for example, treating the bacteria by ultraviolet irradiation, or with a mutagenizing agent, followed by selection of the resultant mutant strain. Mutagenizing agents which are useful in the present invention include N-methyl-N'-nitro-N-nitrosoguanidine (NTG) or nitrous acid. Methods other than mutagenesis treatments for obtaining a coryneform bacteria having reduced GLS activity include gene disruption. That is, a coryneform bacterium is transformed with a DNA containing a gls gene whereby a partial sequence of the gls gene is deleted so as to disrupt GLS function (deletion-type gls gene), and the subsequent recombination between the deletion-type gls gene and the gls gene on the chromosome disrupts the gls gene on the chromosome. Such gene disruption by gene substitution via homologous recombination is known, as well as methods of utilizing linear DNA, methods of utilizing a plasmid containing a temperature sensitive replication origin, and so forth.

Attenuation of the GLS activity can also be accomplished by replacing an expression regulatory sequence such as gls gene promoter with a weaker one (Japanese Patent Laid-open No. 2000-818935). The mutatagenesis methods and the gene disruption methods may be used in combination.

A gls gene on a host chromosome can be replaced with the deletion-type gls gene, for example, in the following manner. A recombinant DNA is prepared by inserting a temperature-sensitive replication origin, the deletion-type gls gene and a marker gene for resistance to a drug such as chloramphenicol, and used to transform a coryneform bacterium. Then, the resultant transformant is cultured in the medium containing the drug so that the temperature-sensitive replication origin does not function, and, as a result, a transformant is obtained in which the recombinant DNA has been incorporated into the chromosomal DNA.

To introduce the recombinant DNA prepared as described above into a coryneform bacterium, any known transformation method can be employed. For instance, such methods include treating recipient cells with calcium chloride so as to increase the permeability of the cells for DNA, which has been reported for *Escherichia coli* K-12 (Mandel, M. and Higa, A., J. Mol. Biol., 53, 159 (1970)), and preparing competent cells from cells which are at the growth phase followed by introducing the DNA thereinto, which has been reported for *Bacillus subtilis* (Duncan, C. H., Wilson, G. A. and Young, F. E., Gene, 1, 153 (1977)). Furthermore, a method of making DNA-recipient cells into protoplasts or spheroplasts, which can easily take up recombinant DNA, followed by introducing the recombinant DNA into the DNA-acceptor cells, which is known to be applicable to *Bacillus subtilis*, actinomycetes and yeasts (Chang, S. and Choen, S. N., Molec. Gen. Genet, 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929(1978)) can be also employed. The transformation of coryneforum bacteria can also be performed by the electric pulse method (Sugimoto et al., Japanese Patent Laid-open No. 2-207791).

Examples of the temperature-sensitive plasmid for coryneform bacteria include, but are not limited to p48K and pSFKT2 (see Japanese Patent Laid-open No. 2000-262288 for these), pHSC4 (see France Patent Laid-open No. 2667875, 1992 and Japanese Patent Laid-open No. 5-7491) and so forth. These plasmids can autonomously replicate at 25° C. at least, but cannot autonomously replicate at 37° C. The *Escherichia coli* AJ12571 harboring pHSC4 was deposited at the National Institute of Bioscience and Human-Technology, the Agency of Industrial Science and Technology, the Ministry of International Trade and Industry (currently, the independent administrative corporation, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-5466)) on Oct. 11, 1990, receiving an accession number of FERM P-11763. Then, the deposit was converted into an international deposit under the provisions of the Budapest Treaty on Aug. 26, 1991, receiving an accession number of FERM BP-3524. Furthermore, it is also possible to transform a coryneform bacterium with a plasmid that cannot autonomously replicate in coryneform bacteria and incorporate the plasmid into the chromosome of the coryneform bacterium by homologous recombination, as described in the examples section.

In a strain incorporating recombinant DNA into chromosomal DNA as described above, the deletion-type gls is recombined with the native gls sequence present on the chromosome, and the chromosomal gls and the deletion-type gls are inserted into the chromosome so that the other portions of the recombinant DNA (vector segment, temperature sensitive replication origin and drug resistance marker) are present between the two genes. Therefore, the transformant strain expresses native gls, because the native gls is dominant in this state.

Then, so that only the deletion-type gls remains on the chromosomal DNA, one copy of gls is eliminated from the chromosomal DNA with the vector segment (including the temperature sensitive replication origin and the drug resistance marker) by recombination of two of gls genes. In this case, the normal gls is left on the chromosomal DNA, and the deletion-type gls is excised from the chromosomal DNA, or vice versa. In the both cases, the excised DNA may be retained in the cell as a plasmid when the cell is cultured at a temperature at which the temperature sensitive replication origin can function. Subsequently, if the cell is cultured at a temperature at which the temperature sensitive replication origin cannot function, gls on the plasmid is eliminated along with the plasmid from the cell. Then, a strain in which gls is disrupted can be obtained by selecting a strain in which the deletion-type gls is left on the chromosome by using PCR, Southern hybridization or the like.

It is sufficient that the deletion-type gls gene used for the gene disruption should have a homology to the target gls gene on the chromosomal DNA of the coryneform bacterium to such a degree that homologous recombination results. The homology is preferably 70% or more, more preferably 80% or more, still more preferably 90% or more, and most preferably 95% or more. Furthermore, DNAs that can hybridize with each other under stringent conditions may cause homologous recombination. The "stringent conditions" include conditions under which a so-called specific hybrid is formed, and a non-specific hybrid is not formed. It is difficult to clearly express this condition by using any numerical value. However, for example, the stringent conditions include conditions whereby DNAs hybridize with each other at a salt concentration typically used for washing in Southern hybridization, i.e., 1×SSC, 0.1% SDS, preferably 0.1×SSC, 0.1% SDS, at 60° C.

It is assumed that in the cells of coryneform bacteria, L-glutamine is synthesized by glutamine synthetase ("GS"), and degraded by glutaminase ("GLS"). That is, the inventors of the present invention deduced that to efficiently produce L-glutamine in high yields, it was important to maintain the GS activity at a high level, while keeping the GLS activity at a low level. However, in stains of coryneform bacteria, the GS activity is remarkably lower than the GLS activity. It is needless to say that, although the equilibrium of intracellular L-glutamine formation and degradation in cells during L-glutamine production is changed with not only specific activities of these enzymes, but also with Km values of the enzymes and intracellular concentrations of substrates, the specific activities represent an important factor.

For example, as described in Example 4, in a mutant strain having reduced GLS activity, the L-glutamine yield is increased when the residual GLS activity is suppressed to a level of about 60 percent of the GS activity.

The GS activity can be measured, for example, as follows. The reaction by GS can be quantified by adding a crude enzyme solution of a coryneform bacterium to a solution containing 100 mM imidazole-HCl (pH 7.0), 90 mM KCl, 0.1 mM $NH_4Cl$, 1 mM $MnCl_2$, 1 mM phosphoenolpyruvic acid, 0.3 mM NADH, 10 U of lactate dehydrogenase, 25 U of pyruvate kinase, 1 mM ATP and 10 mM MSG (sodium glutamate), and measuring variation of absorbance at 340 nm at 30° C. For the measurement of blank, the aforementioned reaction solution without the MSG is used. The protein concentration of the crude enzyme solution is quantified by using Protein Assay (Bio-Rad) with bovine serum albumin as a standard sample. In the present invention, the amount of enzyme necessary to produce 1 μmol of NAD per minute in the aforementioned reaction system is defined as 1 U. Hereafter, the GS activity per 1 mg of protein is indicated with a unit of "U/mg".

The aforementioned crude enzyme solution is prepared, for example, as follows. That is, the crude enzyme solution is prepared by separating cells from the culture broth by centrifugation, washing the cells with 100 mM imidazole-HCl (pH 7.0, a solution containing 90 mM KCl), sonicating the cells and removing insoluble fraction by ultracentrifugation.

In order to efficiently produce L-glutamine by using the coryneform bacterium of the present invention, a strain in which the GLS activity is reduced and the glutamine synthetase activity is enhanced simultaneously is preferably used.

The expression "glutamine synthetase activity is enhanced" means that the GS activity per cell is higher than that of a coryneform bacterium. For example, it can be exemplified by a case where the number of GS molecules per cell increases, and a case where the GS activity per GS molecule increases and so forth. Furthermore, a coryneform bacterium that serves as an object for comparison may be, for example, the *Brevibacterium flavum* ATCC 14067. As a result of enhancement of the GS activity, the amount of L-glutamine accumulation in a medium increases, and the L-glutamic acid by-product decreases, and so forth, can be obtained.

It is sufficient that in the coryneform bacterium of the present invention, the GLS activity is reduced, and the GS activity is enhanced as compared with a strain or unmodified strain. Preferably, the coryneform bacterium of the present invention is a bacterium in which the GLS activity should be similar to or less than the GS activity, more preferably the GLS activity should be ½ or less of the GS activity, when measured as activity per unit weight of cellular proteins. In the present invention, the GLS activity and GS activity per unit weight of cellular protein mean the activities measured by the aforementioned measurement methods and defined according to the aforementioned definitions.

Enhancing the GS activity in a coryneform bacterium can be attained by increasing the copy number of the gene encoding GS. For example, a recombinant DNA can be prepared by ligating a gene figment encoding GS with a vector known to function in the bacterium, preferably a multi-copy type vector, and transform the vector into a host having L-glutamine-producing ability. Alternatively, the aforementioned recombinant DNA can be introduced into a coryneform bacterium to obtain a transformant, and the L-glutamine-producing ability can be subsequently imparted to the transformant.

Any of genes derived from coryneform bacteria, or genes derived from other organisms such as bacteria belonging to the genus *Escherichia* can be used as the GS gene. Among these, genes derived from coryneform bacteria are preferred for their ease of expression.

The glnA gene is known to encode GS of coryneform bacterium (FEMS Microbiology Letters, 154, 81-88, 1997). The GS gene can be obtained by PCR using primers based on the known nucleotide sequence, for example, the primers shown in SEQ ID NOS: 19 and 20, and using chromosomal DNA of a coryneform bacterium as a template. Genes encoding GS from other microorganism can also be similarly obtained. The nucleotide sequence of the gln4 gene of the *Brevibacterium flavum* ATCC 14067 stain and the amino acid sequence encoded thereby are shown in SEQ ID NOS: 3 and 4.

The gene encoding GS may be, besides the gln gene, one encoding an amino acid sequence which includes substitution, deletion, insertion, addition or inversion of one or several amino acids, so long as the encoded GS has the activity of catalyzing the reaction of L-glutamic acid and ammonium ion to produce L-glutamine. The number of "several" amino acids as used herein varies depending on the positions of amino acid residues in the three-dimensional structure of the protein and the types of the amino acids. However, it preferably means between 2 to 30, more preferably between 2 to 20, and most preferably between 2 to 10.

Examples of DNA encoding substantially the same protein as GS described above include DNA which is hybridizable with a probe having the sequence of nucleotide numbers of 874 to 2307 of the nucleotide sequence shown in SEQ ID NO: 3 or a probe prepared from this nucleotide sequence under stringent conditions, and encodes a protein having an activity similar to GS. The "stringent conditions" include conditions in which a so-called specific hybrid is formed, and a non-specific hybrid is not formed. It is difficult to clearly express this condition by using any numerical value. However, for example, the stringent conditions include a condition whereby DNAs having high homology, for example, DNAs having homology of 70% or more, preferably 80% or more, more preferably 90% or more, still more preferably 95% or more, hybridize with each other, whereas DNAs having homology lower than the above do not hybridize with each other. Alternatively, the stringent conditions are exemplified by conditions whereby DNAs hybridize with each other at a salt concentration typical for washing in Southern hybridization, i.e., 1×SSC, 0.1% SDS, preferably 0.1×SSC, 0.1% SDS, at 60° C.

A vector that functions in coryneform bacteria means, for example, a plasmid that can autonomously replicate in coryneform bacteria Specific examples thereof include, but are not limited to the pAM330 (see Japanese Patent Laid-pen No. 58-67699), pHM1519 (see Japanese Patent Laid-open No. 58-77895), pSFK6 (see Japanese Patent Laid-open No. 2000-262288)

If a DNA fragment having an ability to make a plasmid autonomously replicable in coryneform bacteria is removed from these vectors and inserted into the aforementioned vectors for *Escherichia coli*, they can be used as a so called shuttle vector autonomously replicable in both of *Escherichia coli* and coryneform bacteria.

Examples of such a shuttle vector include, but are not limited to those described herein. Bacterial strains that harbor each of the vectors and accession numbers thereof at the intenational depositories in the parentheses are as follows:

pAJ655 *Escherichia coli* AJ11882 (FERM BP-136)
   *Corynebacterium glutamicum* SR8201 (ATCC 39135)
pAJ1844 *Escherichia coli* AJ11883 (FERM BP-137)
   *Corynebacterium glutamicum* SR8202 (ATCC 39136)
pAJ611 *Escherichia coli* AJ11884 (FERM BP-138)
pAJ3148 *Corynebacterinum glutamicum* SR8203 (ATCC 39137)
pAJ440 *Bacillus subtilis* AJ 1901 (FERM BP-140)
pHC4 *Escherichia coli* AJ12617 (FERM BP-3532)

These vectors can be obtained from the deposited bacteria as follows. That is, cells collected in their exponential growth phase are lysed using lysozyme and SDS, and centrifuged at 30000×g. The supernatant obtained from the lysate is added with polyethylene glycol, fractionated and purified by cesium chloride-ethidium bromide equilibrium density gradient centrifugation.

The copy number of the GS gene can also be increased by allowing multiple copies of the gene to exist on chromosomal DNA of a coryneform bacterium. This can be performed by targeting a sequence present on chromosomal DNA in multiple copy number. A repetitive DNA or an inverted repeat present at the end of a transposable element can be used as the sequence present on chromosomal DNA in multiple copy number. Alternatively, as disclosed in Japanese Patent Laid-open No. 2-109985, multiple copies of the GS gene can be introduced into chromosomal DNA by incorporating them into a transposon and transferring it.

Besides the above gene amplification methods, expression of the GS gene can be enhanced by replacing an expression control sequence, such as promoters of GS gene, with a stronger one. Examples of strong promoters include lac promoter, trp promoter, tm promoter and so forth. Moreover, it is also possible to introduce nucleotide substitutions for several nucleotides into a promoter region of the GS gene so that it is modified into a stronger one, as disclosed in International Patent Publication WO00/18935. By such substitution or modification of the promoter region, expression of the GS gene is enhanced, and thus the GS activity is enhanced. Such modification of expression regulatory sequence may be combined with the increase of copy number of the GS gene.

For example, the transcription initiation site of the glnA gene of coryneform bacteria as well as its promoter region have been reported by Anton et al. (FEMS Microbiogy Letters, 205, 361-367, 2001). For example, the GS activity is enhanced by replacing the sequence of −10 region with TATAAT, and −35 region of the GS gene with TTGCCA, which regions are disclosed in FIG. 3C of the aforementioned reference. However, in the present invention, the −35 to −30 region of the GS gene means a site which is located 3 bp downstream, i.e., toward transcription initiation site, from −35 to −30 region described in the aforementioned reference (nucleotide numbers 727 to 732 in SEQ ID NO: 3). On the other hand, the −10 region of the GS gene means a site which is the same as −10 region described in the aforementioned reference (nucleotide numbers 751 to 756 in SEQ ID NO: 3). Such modifications of these regions of the GS gene can be performed by, for example, site-specific mutagenesis.

Examples of the GS gene where the −35 region and −10 region are modified include, but are not limited to the glnA gene of coryneform bacteria, for example, a gene having the sequence of SEQ ID NO: 3. The encoded protein may have an amino acid sequence including substitution, deletion, insertion, addition, or inversion of one or several amino acid residues so long as the encoded protein has an activity of catalyzing the reaction generating L-glutamine from an ammonium ion and L-glutamic acid.

Besides increase of expression of the GS gene described above, the GS activity can also be enhanced by eliminating the activity control via the adenylylation of intracellular GS (US Pat App Pub No. 2003/0003550A1)

In the coryneform bacterium of the present invention, besides reduction of the GLS activity and enhancement of the GS activity, an activity of an enzyme catalyzing a reaction involved in the L-glutamine biosynthesis pathway may be enhanced. Examples of the such an enzyme include, but are not limited to isocitrate dehydrogenase, aconitate hydratase, citrate synthase, pyruvate dehydrogenase, phosphoenolpyruvate carboxylase, pyruvate carboxylase, pyruvate kinase, phosphofructokinase and so forth.

Furthermore, activity of an enzyme that catalyzes a reaction branching off from the L-glutamine biosynthesis pathway and producing a compound other than L-glutamine may be reduced or eliminated. Examples of such an enzyme include, but are not limited to isocitrate lyase, α-ketoglutarate dehydrogenase, glutamate synthase and so forth.

Production of L-Glutamine Using Microorganism of the Present Invention

L-glutamine can be efficiently produced and the L-glutamic acid by-product can be suppressed by culturing a coryneform bacterium obtained as described above in a medium. L-glutamate is produced, and accumulates in the medium and may be collected from the medium.

In order to produce L-glutamine by using the coryneform bacterium of the present invention, culture can be performed in a conventional manner using a typical medium containing a carbon source, nitrogen source and mineral salts as well as organic trace nutrients such as amino acids and vitamins, as required. Either a synthetic medium or a natural medium may be used. Any kind of carbon source and nitrogen source may be used so long as they can be utilized by the strain to be cultured.

Sugars such as glucose, glycerol, fructose, sucrose, maltose, mannose, galactose, starch hydrolysates and molasses, and organic acids such as acetic acid and citric acid, and alcohols such as ethanol can also be used each alone or in a combination with other carbon sources as the carbon source.

Ammonia, ammonium salts such as ammonium sulfate, ammonium carbonate, ammonium chloride, ammonium phosphate and ammonium acetate, nitric acid salts and so forth can be used as the carbon source.

Amino acids, vitamins, fatty acids, nucleic acids, those containing those substances such as peptone, casamino acid, yeast extract and soybean protein decomposition product and so forth can be used as the carbon source. It is preferable to supplement the required nutrient when an auxotrophic mutant strain that requires an amino acid or the like for its growth is used.

Phosphoric acid salts, magnesium salts, calcium salts, iron salts, manganese salts and so forth can be used as the mineral salts.

The culture may be performed with aeration. The culture temperature is controlled to be 20 to 45° C., and pH is controlled to be 5 to 9. When pH falls during the culture, the medium can be neutralized by addition of calcium carbonate or an alkali such as ammonia gas or the like. A substantial amount of L-glutamine is accumulated in the culture broth after 10 to 120 hours of culture in such a manner as described above.

L-glutamine can usually be collected from the culture broth after the culture in a conventional manner. For example, after the cells were removed from the culture broth, L-glutamine can be collected by concentrating the broth to crystallize L-glutamine.

EXAMPLES

Hereinafter, the present invention will be explained more specifically with reference to the preferred embodiments, given only by way of example.

Example 1

Constructions of gls-Amplified Strain (1) Measurement of Glutaminase Activity of Coryneform Bacterium Existence of glutaminase, an enzyme that degrades L-glutamine to generate L-glutamic acid, had not been definitely reported in coryneform bacteria. Therefore, the inventors of the present invention verified whether the glutaminase activity existed in coryneform bacteria.

The $Brevibacterium\ flavum$ ATCC 14067 strain was inoculated into a medium containing 30 g of glucose, 1.5 g of $KH_2PO_4$, 0.4 g of $MgSO_4.7H_2O$, 0.01 g of $FeSO_4.7H_2O$, 100 µg of $VB_1$.HCl, 3 µg of biotin, 200 mg of soybean hydrolysates, 1.5 g of urea and 0.02 ml of anti-foam agent GD-113 in 1 L of pure water (adjusted to pH 7.0 with KOH) and cultured at 31.5° C. with shaking. The cells were separated from the culture broth by centrifugation, washed with 100 mM Tris-HCl (pH 8.0) and disrupted by sonication. The undisrupted cells were removed by centrifugation to obtain a crude enzyme solution The protein concentration in the crude enzyme was quantified by using Protein Assay (Bio-Rad) with bovine serum albumin as a standard sample.

The glutaminase activity was measured by adding the crude enzyme solution to a solution containing 100 mM Tris-HCl (pH 8.0) and 75 mM L-glutamine, allowing a reaction at 30° C. for 30 minutes or 60 minutes, then adding SDS at a final concentration of 0.5% to terminate the reaction, and quantifying the produced L-glutamic acid. As a result, it was demonstrated that an enzyme exhibiting the glutaminase activity was present in $Brevibacterium\ flavum$ as shown in Table 1.

TABLE 1

| GLS activity of coryneform bacterium | |
| --- | --- |
| Strain | GLS (U/mg) |
| ATCC 14067 | 0.25 |

(2) Cloning of Glutaminase Gene

It is known that L-glutamine serves as a donor of $NH_3$ in the biosyntheses of nucleic acids, amino acids etc., and that the small subunit of carbamoylphosphate synthetase exhibits the glutaminase activity. Furthermore, a gene encoding glutaminase, glsA, was recently cloned for $Rhizobium\ etli$ and characterized as providing the glutaminase activity independently from the nucleic acid and amino acid biosyntheses (Biochim. Biophys. Acta., 1444(3): 451-6, 1999). Therefore, the inventors of the present invention searched genes of $Corynebacterium\ glutamicum$ for a homologous gene to glsA, and as a result, they found a gene which was estimated to encode GLS. Then, based on the nucleotide sequence of the putative GLS gene, the homologue of the gene was cloned and amplified in $Brevibacterium\ flavum$, and improved glutaminase activity was verified The nucleotide sequence of the cloned gene is shown in SEQ ID NO: 1 (hereafter; a gene having the nucleotide sequence of SEQ ID NO: 1 is referred to as "gls").

The target sequence was amplified by PCR using the primers shown in SEQ ID NOS: 5 and 6, and using the chromosomal DNA of *Brevibacterium flavum* ATCC 14067 strain as a template. The sequences of SEQ ID NOS: 5 and 6 correspond to the nucleotide numbers 1 to 20 and 2100 to 2081 of SEQ ID NO: 1, respectively. The chromosomal DNA of *Brevibacterium flavum* ATCC 14067 strain was prepared using Bacterial Genome DNA Purification Kit (Advanced Genetic Technologies Corp.). PCR was performed for 30 cycles each consisting of denaturation at 94° C. for 30 seconds, annealing at 55° C. for 15 seconds and extension at 72° C. for 3 minutes by using Pyrobest DNA Polymerase (Takara Shuzo).

The resulting PCR product was purified in a conventional manner and blunt-ended using Blunting Kit (Takara Shuzo). The blunt-ended PCR product was ligated by using Ligation Kit (Takara Shuzo) with a shuttle vector for coryneform bacteria and *Escherichia coli*, pHMK2, which had been digested with SmaI. The ligation mixture was used to transform competent cells of *Escherichia coli* JM109 (Takara Shuzo). The cells were plated on L medium containing 10 μg/ml of IPTG, 40 μm of X-Gal and 25 μg/ml of kanamycin and cultured overnight. Then, the emerged white colonies were selected and separated into single colonies to obtain transformants. Plasmids are prepared from the transformants by the alkali method and a plasmid in which the objective PCR fragment was inserted into the vector was isolated. The obtained plasmid was designated as pHMKGLS5.

The aforementioned pHMK2 was obtained as follows. The plasmid pHK4 (see Japanese Patent Laid-open No. 5-7491) having a replication origin derived from the plasmid pHM1519 autonomously replicable in coryneform bacteria (Agric. Biol. Chem., 48, 2901-2903 (1984)) was digested with the restriction enzymes BamHI and SmaI to obtain a fragment containing the replication origin. The obtained fragment was blunt-ended by using DNA Blunting Kit (Takara Shuzo), and inserted into the BsaAI site of the cloning vector pK1 for *E. coli* (Japanese Patent Laid-open No. 2000-262288) to obtain pHMK2. The construction process of pHMKGLS5 is shown in FIG. 1.

(3) Construction of gls-Overexpressing Stain pHMGLS5 obtained in (2) described above was introduced into a coryneform bacterium to obtain a gls-amplified strain. Specifically, the *Brevibacterium flavum* ATCC 14067 strain was transformed with pHMGLS5 by the electric pulse method (see Japanese Patent Laid-open No. 2-207791), plated on CM2G medium (10 g/L of polypeptone, 10 g/L of yeast extract, 5 g/L of NaCl, 1 g/L of glucose, pH 7.0 (KOH)) containing 25 μg/ml of kanamycin, and cultured at 31.5° C. for two days. The emerged colony was isolated as a transformant and designated as 2247/pHNKGLS5. A pHMK-introduced strain was also constructed, and the obtained transformant was designated as 2247/pHMK2. These transformants were each cultured by the method described in (1), and the GLS activity was measured. As a result, it was confirmed that the glutaminase activity increased in the pHMGLS5-introduced strain (Table 2). The plasmid-harboring ratio of the transformants was 100%.

TABLE 2

| GLS activity of GLS-amplified strain | |
|---|---|
| Strain | GLS (U/mg) |
| ATCC14067/pHMK2 | 0.19 |
| ATCC14067/pHMKGLS5 | 0.33 |

Example 2

Construction of gls-Deficient Strain (1) Construction of Plasmid for Disruption of gls In order to confirm whether any gene encoding glutaminase of coryneform bacteria other than the gls gene might exist, a gls-deficient strain was constructed. The method is specifically described herein.

First, PCR was performed by using the chromosomal DNA of *Brevibacterium flavum* ATCC 14067 stain as a template and the synthetic DNAs of SEQ ID NOS: 5 and 7 as primers to obtain an amplification product of the N-terminus side of the gls gene. Then, in order to obtain an amplification product of a sequence of the C-terminus side of the gls gene, PCR was performed using the chromosomal DNA of *Brevibacterium flavum* ATCC 14067 stain as a template and the synthetic DNAs of SEQ ID NOS: 6 and 8 as primers. The sequences of SEQ ID NOS: 7 and 8 are partially complementary to each other. The sequences of SEQ ID NOS: 7, 8, 9, and 10 correspond to the nucleotide numbers 1245 to 985, 983 to 1245, 414 to 438, and 1869 to 1845 of SEQ ID NO: 1, respectively, and the sequences of SEQ ID NOS: 7 and 8 are deficient in the nucleotides of the nucleotide numbers 1003 to 1230 of SEQ ID NO: 1. PCR was performed by using Z-Taq (Takara Shuzo) for 30 cycles each consisting of denaturation at 94° C. for 30 seconds, annealing at 55° C. for 15 seconds and extension at 72° C. for 30 seconds.

Then, in order to obtain a gls gene fragment having an internal sequence deleted, the aforementioned gene fragments of the N- and C-terminus sides were mixed in substantially equimolar amounts, and PCR was performed using this mixture as a template and the synthetic DNAs of SEQ ID NOS: 9 and 10 as primers to obtain a gls gene amplification product having a mutation. PCR was performed using Z-Taq (Takara Shuzo) for 30 cycles each consisting of denaturation at 94° C. for 30 seconds, annealing at 55° C. for 15 seconds and extension at 72° C. for 30 seconds. This gls gene product has the amino acid sequence of SEQ ID NO: 2 whereby the 110th to 185th amino acids are deleted.

Figure 2:
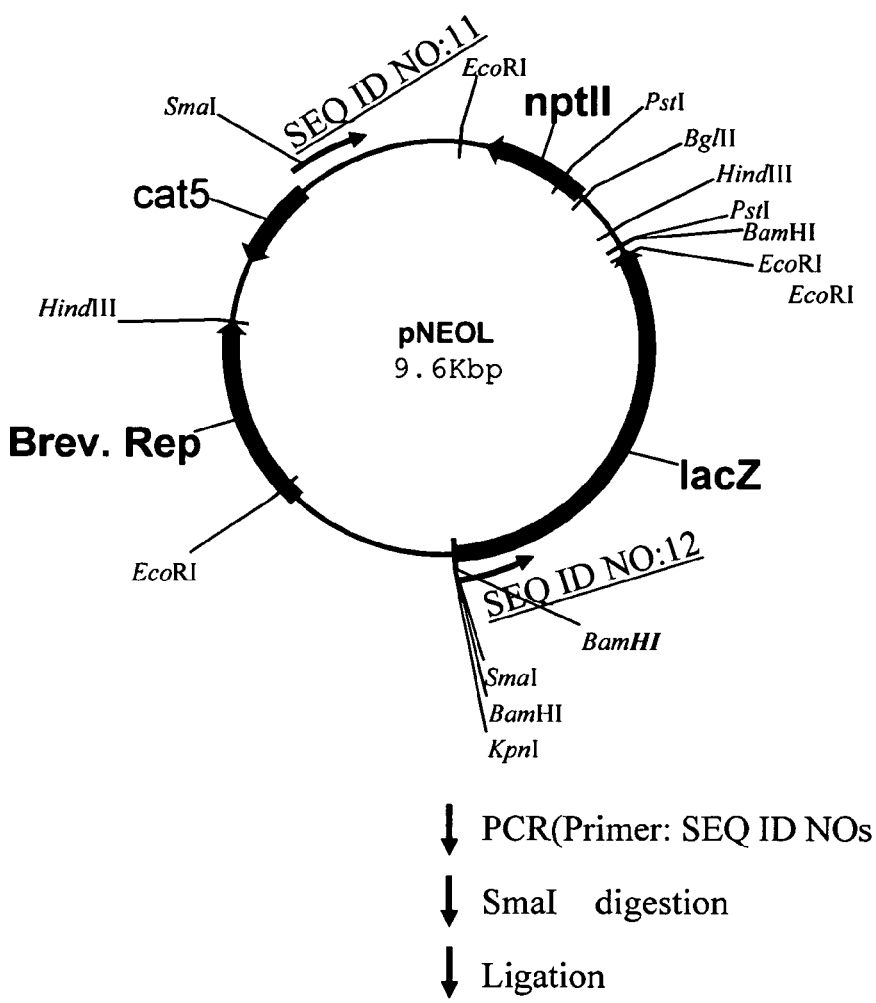
FIG. 2 shows scheme for construction of plasmid pNEL not containing any region autonomously replicable in coryneform bacteria.
Figure 2:
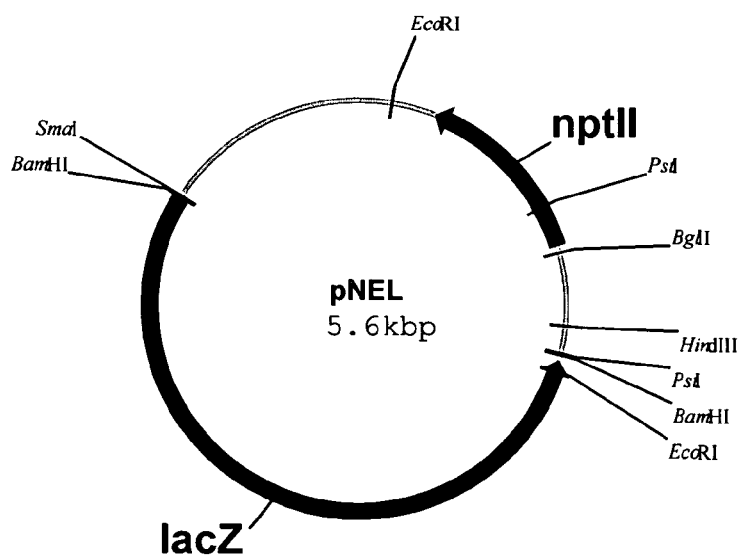
Figure 3:
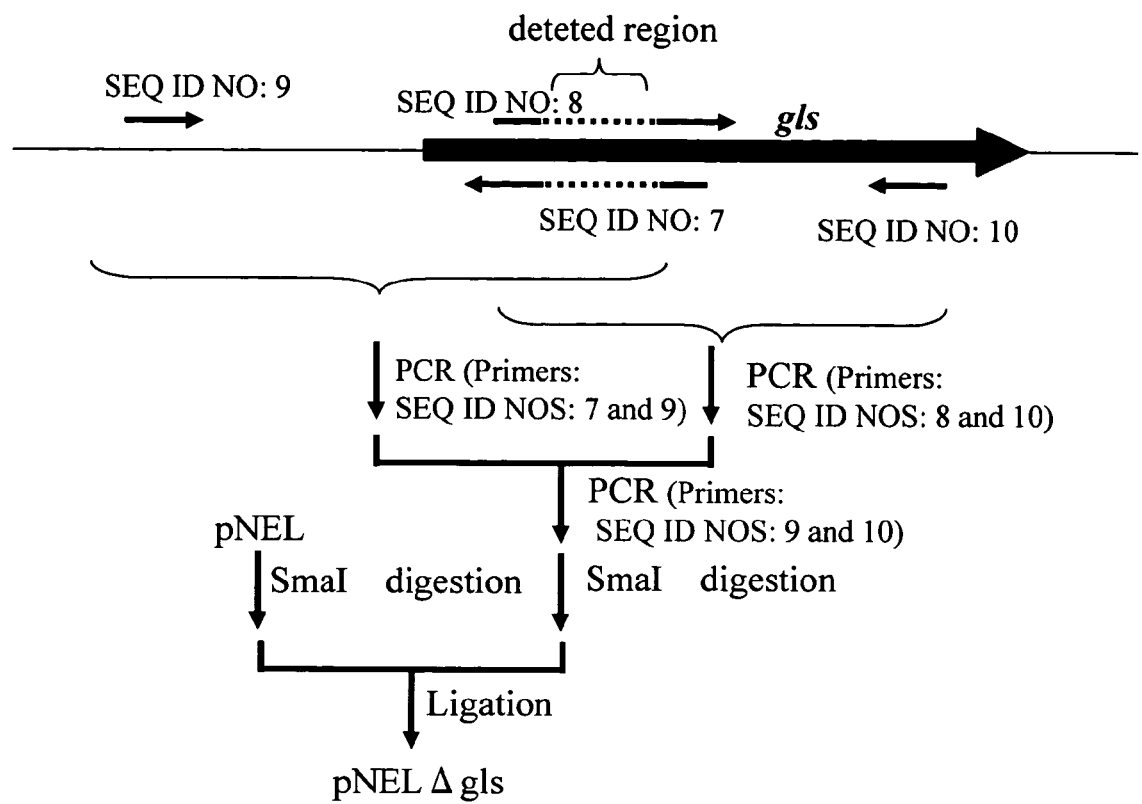
FIG. 3 shows scheme for construction of plasmid pNELΔgls for disruption of gls.

The resultant PCR product was purified in a conventional manner, then digested with SmaI and inserted into the SmaI site of pNEL. By using this DNA, competent cells of *Escherichia coli* DH5α (Takara Shuzo) were transformed, and the cells were applied to L medium containing 40 μg/ml of X-Gal and 25 μg/ml of kanamycin and cultured overnight. Then, the emerged blue colonies were picked up, and separated into single colonies to obtain transformant strains. Plasmids were extracted from the obtained transformants, and the plasmid inserted with the target PCR product was designated as pNELΔgls.

pNEL is a plasmid obtained by performing PCR using pNEOL (see WO00/18935) as a template and the synthetic DNAs shown in SEQ ID NOS: 11 and 12 as primers, digesting the amplification product with SmaI and self-ligating the digestion product The plasmid pNEL does not contain any region autonomously replicable in the cells of coryneform bacteria PCR was performed by using Pyrobest DNA Polymerase (Takara Shuzo) for 30 cycles each consisting of denaturation at 98° C. for 20 seconds, annealing and extension at 68° C. for 6 minutes. The construction scheme of pNEL is shown in FIG. 2, and the construction scheme of pNELΔgls is shown in FIG. 3.

(2) Construction of gls-Deficient Strain pNELΔgls obtained in (1) does not contain a region autonomously replicable in the cells of coryneform bacteria. Therefore, if a coryneform bacterium is transformed with this plasmid, a strain having this plasmid introduced into the chromosome by homologous recombination would appear as a transformant although it occurs at an extremely low frequency. The *Brevibacterium flavum* ATCC 14067 strain was transformed with a high concentration of pNELΔgls by the electric pulse method, plated on CM2G medium (10 g/L of polypeptone, 10 g/L of yeast extract, 5 g/L of NaCl, 1 g/L of glucose, pH 7.0 (KOH)) containing 25 g/ml of kanamycin, and cultured at 31.5° C. for two days, and the emerged colony was isolated as a transformant. This transformant forms a blue colony on the CM2G plate containing 40 μg/ml of X-Gal. Then, this transformant was subcultured in CM2G medium not containing kanamycin, appropriately diluted and then applied to a CM2G plate containing 40 μg/ml of X-Gal. From a large number of emerged colonies, the strains that formed a white colony and showed kanamycin (km) sensitivity were chosen.

PCR was performed using the chromosomal DNA of these Km sensitive strains as a template and synthetic DNAs of SEQ ID NOS: 5 and 6 as primers, and a strain that provided a PCR product having a size smaller than that obtained using the chromosomal DNA of ATCC 14067 as a template was used for the following experiments as a gls-deficient strain (hereinafter, 2247Δgls).

(3) Introduction of gls Plasmid into 2247Δgls

The plasmid pGLS5 described in Example 1, section (2) was introduced into the 2247Δgls strain obtained in (2) described above by the electric pulse method, and a transformant was obtained by using the kanamycin resistance as a marker. The obtained transformant was designated as 2247Δgls/pGLS5. Separately, pHMK2 was also introduced, and the obtained transformant was designated as 2247Δgls/pHMK2.

(4) Measurement of GLS Activity of gls-Deficient Stain

The result of GLS activity measurement performed by the method described in Example 1, (1) for *Brevibacterium flavum* ATCC 14067, 2247Δgls and pHMK2 and pHMKGLS-introduced strains thereof are shown in Table 3. It was confirmed that the activity to degrade L-glutmine had almost disappeared in 2247Δgls. Furthermore, the disappearance of the activity was complemented by the introduction of pHMKGLS5. Thus, it was deduced that the gene mainly responsible for the glutaminase activity of coryneform bacteria is gls.

TABLE 3

GLS activity of GLS-deficient strain and strain complemented with plasmid

| Strain | GLS activity(U/mg) |
|---|---|
| 2247Δgls | 0.003 |
| 2247Δgls/pHMK2 | 0.000 |
| 2247Δgls/pHMKGLS5 | 0.19 |

Example 3

Production of L-Glutamine by gls-Deficient Strain (1) Evaluation of Culture of gls-Deficient Strain L-glutamine was produced by *Brevibacterium flavum* ATCC 14067 strain and 2247Δgls strain as follows. Cells of the *Brevibacterium flavum* ATCC 14067 strain and the 2247Δgls strain obtained by culture on a CM2B plate medium were each inoculated into a medium containing 100 g of glucose, 60 g or 40 g of $(NH)_2SO_4$, 2.5 g of $KH_2PO_4$, 0.4 g of $MgSO_4 \cdot 7H_2O$, 0.01 g of $FeSO_4 \cdot 7H_2O$, 350 μg of $VB_1 \cdot HCl$, 4 μg of biotin, 200 mg of soybean hydrolysates and 50 g of $CaCO_3$ in 1 L of pure water (adjusted to pH 6.8 with NaOH) and cultured at 31.5° C. with shaking until the sugar in the medium was consumed.

After the completion of the culture, the amount of accumulated L-glutamine in the culture broth was analyzed for appropriately diluted culture broth by liquid chromatography. CAPCELL PAK C18 (Shiseido) was used as a column, and the sample was eluted with an eluent containing 0.095% phosphoric acid, 3.3 mM heptanesulfonic acid and 5% acetonitrile in 1 L of distilled water. The accumulated L-glutamine (Gln) amount was analyzed based on variation of absorbance at 210 nm. Furthermore, the accumulated L-glutamic acid (Glu) amount was analyzed for appropriately diluted culture broth by using Biotech Analyzer AS210 (Asahi Chemical Industry). The results of the above analysis are shown in Table 4 (60 μL of ammonium sulfate) and Table 5 (40 g/L of ammonium sulfate).

As for the 2247Δgls strain, about 3% of improvement in the yield was recognized for all of the conditions compared with the parent strain, the ATCC 14067 strain. These results demonstrated that disappearance or reduction of the GLS activity was effective for production of L-glutamine.

TABLE 4

L-Glutamine production by GLS activity-reduced strain (1)

| Strain | $OD_{620}$ (X101) | Gln (g/L) | Glu (g/L) | Gln yield (%) |
|---|---|---|---|---|
| ATCC 14067 | 0.398 | 9.9 | 33.4 | 9.7 |
| 2247Δgls | 0.427 | 13.2 | 30.0 | 12.8 |

TABLE 5

L-Glutamine production by GLS activity-reduced strain (2)

| Strain | $OD_{620}$ (X101) | Gln (g/L) | Glu (g/L) | Gln yield (%) |
|---|---|---|---|---|
| ATCC 14067 | 0.489 | 6.8 | 42.6 | 6.4 |
| 2247Δgls | 0.492 | 10.1 | 37.6 | 9.5 |

Example 4

Construction of gls-Deficient and GS Activity Enhanced Strain (1) Construction of Plasmid Having GS Gene with Enhanced Expression The nucleotide sequence of the GS gene of coryneform bacteria has been already elucidated (Genbank Accession No. Y13221). By referring to this sequence, a GS gene with enhanced expression (enhanced-type GS gene) was constructed The method will be specifically described herein. First, primary PCR was performed for the N-terminus side using the chromosomal DNA of *Brevibacterium flavum* ATCC 14067 strain as a template and DNAs of SEQ ID NOS: 13 and 18 as primers, and primary PCR for the C-terminus side was performed using DNAs of SEQ ID NOS: 15 and 17 as primers. The sequences of SEQ ID NOS: 13, 14, 15, 16, 17, and 18 correspond to the nucleotide numbers 487 to 507, 523 to 549, 1798 to 1775, 1770 to 1745, 1118 to 1169, and 1169 to 1118 of Genbank Accession No. Y13221, respectively. The sequences of SEQ ID NOS: 17 and 18 are complementary to each other. PCR was performed by using Pyrobest DNA Polymerase (Takara Shuzo) for 30 cycles each consisting of denaturation at 94° C. for 30 seconds, annealing at 55° C. for 15 seconds and extension at 72° C. for 1 minute.

Then, in order to obtain an enhanced type GS gene fragment, the aforementioned amplification products of the upstream side and downstream side of the GS gene were mixed in substantially equimolar amounts, and PCR was performed using this mixture as a template and the synthetic DNAs of SEQ ID NOS: 14 and 16 as primers to obtain a GS gene amplification product having a mutation PCR was performed by using Pyrobest DNA Polymerase (Takara Shuzo) for 30 cycles each consisting of denaturation at 94° C. for 30 seconds, annealing at 55° C. for 15 seconds and extension at 72° C. for 2 minutes.

Figure 4:
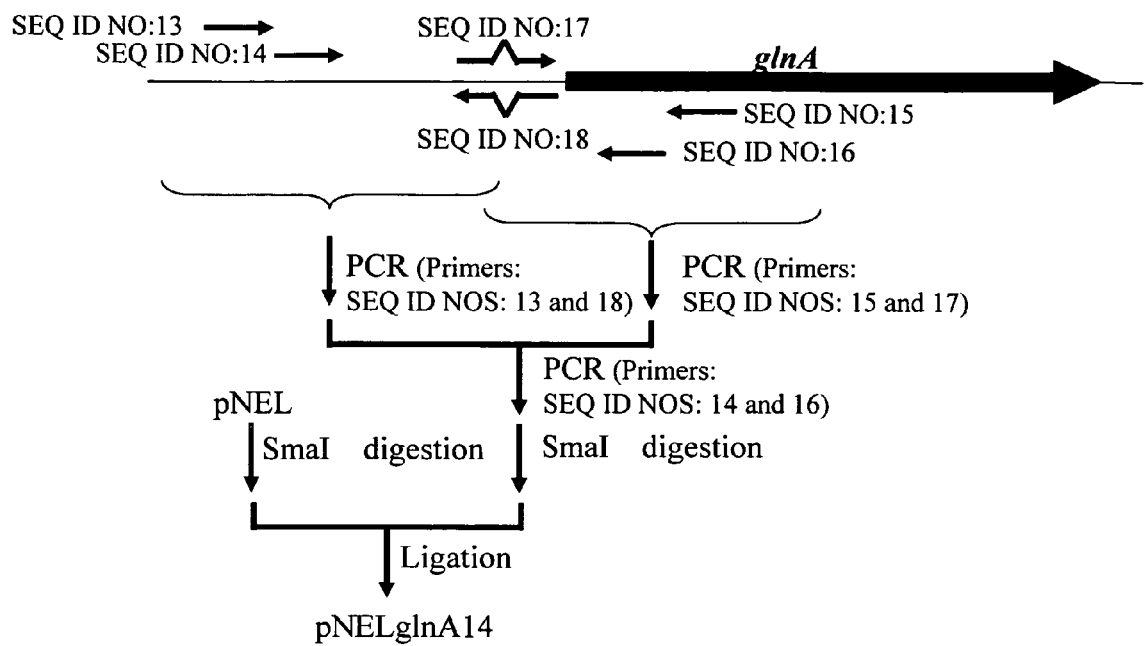
FIG. 4 shows scheme for construction of plasmid pNEL-glnA14 having a GS gene with enhanced expression.

Then, the PCR product was purified in a conventional manner, then digested with SmaI and inserted into the SmaI site of pNEL. Competent cells of *Escherichia coli* DH5α (Takara Shuzo) were transformed with the obtained DNA, and the cells were applied to L medium containing 40 μg/ml of X-Gal and 25 μg/ml of kanamycin and cultured overnight. Then, the emerged blue colonies were picked up, and separated into single colonies to obtain transformants. Plasmids were extracted from the obtained transformants, and the glnA expression regulatory region was sequenced. The plasmid introduced with the objective mutation was designated as pNELglnA14. The construction scheme of pNELglnA14 is shown in FIG. 4. In the glnA gene fragment cloned in pNELglnA14 obtained as described above, the sequence (ATRATA) of the region downstream by 3 bp from the −35 site of the GS gene described in FEMS Microbiogy Letters, 205 (2001) 361-367 is replaced with TATAAT, and the sequence (TTTTGA) of the −10 site is replaced with TTGCCA.

(2) Construction of GS Activity-Enhanced Strain pNELglnA14 obtained (1) described above does not contain any region autonomously replicable in the cells of coryneform bacteria. Therefore, if a coryneform bacterium is transformed with this plasmid, a strain in which this plasmid is introduced into the chromosome by homologous recombination would appear as a transformant although it occurs at an extremely low frequency. The *Brevibacterium flavum* 2247Δgls strain was transformed with a high concentration of pNELglnA14 by the electric pulse method, plated on CM2G medium (10 g/L of polypeptone, 10 g/L of yeast extract, 5 g/L of NaCl, 1 g/L of glucose, pH 7.0 (KOH)) containing 25 μg/ml of kanamycin and cultured at 31.5° C. for two days, and the emerged colonies were isolated as transformants. These transformants form a blue colony on the CM2G plate containing 40 μg/ml of X-Gal. Then, these transformants were subcultured in CM2G medium not containing kanamycin (Km), appropriately diluted and then applied to a CM2G plate containing 40 μg/ml of X-Gal. From a large number of emerged colonies, the strains that formed a white colony and showed kanamycin susceptibility were chosen.

PCR was performed using the chromosomal DNA of these Km sensitive strains as a template and the synthetic DNAs of SEQ ID NOS: 14 and 16 as primers, and the expression regulatory region was sequenced. Among the Km sensitive strains, a strain in which the objective mutation was inserted into the expression regulatory region was isolated. The obtained strain was designated as 2247ΔglsglnA14 and used for the following experiments.

(3) Measurement of GS Activity

The *Brevibacterium flavum* ATCC 14067 strain was inoculated into a medium containing 30 g of glucose, 1.5 g of $KH_2PO_4$, 0.4 g of $MgSO_4 \cdot 7H_2O$, 0.01 g of $FeSO_4 \cdot 7H_2O$, 100 μg of $VB_1 \cdot HCl$, 3 μg of biotin, 350 mg of soybean hydrolysates, 3.0 g of urea and 0.02 ml of GD-113 in 1 L of pure water (adjusted to pH 7.0 with KOH) and cultured at 31.5° C. with shaking. By referring to the method described in Journal of Fermentation and Bioengineering, Vol. 70, No. 3, 182-184, 1990, the GS activity was measured by adding a crude enzyme solution to a solution containing 100 mM imidazole-HCl (pH 7.0), 90 mM KCl, 0.1 mM $NH_4Cl$, 1 mM $MnCl_2$, 1 mM phosphoenolpyruvic acid, 0.3 mM NADH, 10 U of lactate dehydrogenase, 25 U of pyruvate kinase, 1 mM ATP and 10 mM MSG, and measuring variation of absorbance at 340 nm at 30° C. For the measurement of blank, the aforementioned reaction solution not containing MSG was used. The protein concentration of the crude enzyme solution was quantified by using Protein Assay (Bio-Rad) with bovine serum albumin as a standard. It was verified that the GS activity was enhanced about three times in the GS activity enhanced strain.

TABLE 6

GLS and GS activities of GLS-deficient strain and GLS-deficient and GS-enhanced strain

| Strain | GLS activity (U/mg) | GS activity (U/mg) |
|---|---|---|
| ATCC 14067 | 0.19 | 0.019 |
| 2247Δgls | 0.012 | 0.019 |
| 2247Δgls glnA14 | 0.014 | 0.063 |

(4) Evaluation of Culture of GLS Activity-Reduced and GS Activity Enhanced Strain By using the *Brevibacterium flavum* ATCC 14067 strain, 2247Δgls strain, and 2247Δgls glnA14 strain, culture for L-glutamine production was performed as follows. Cells of the *Brevibacterium flavum* ATCC 14067 strain, 2247Δgls strain, and 2247Δgls glnA14 strain obtained by culture on a CM2B plate medium were each inoculated into a medium containing 100 g of glucose, 60 g of $(NH_4)_2SO_4$, 2.5 g of $KH_2PO_4$, 0.4 g of $MgSO_4 \cdot 7H_2O$, 0.01 g of $FeSO_4 \cdot 7H_2O$, 350 μg of $VB_1 \cdot HCl$, 4 μg of biotin, 200 mg of soybean hydrolysates and 50 g of $CaCO_3$ in 1 L of pure water (adjusted to pH 6.8 with NaOH) and cultured at 31.5° C. with shaking until the sugar in the medium was consumed.

After the completion of the culture, the amount of accumulated L-glutamine in the culture broth was analyzed for appropriately diluted culture broth by liquid chromatography. Furthermore, the accumulated L-glutamic acid amount was analyzed for appropriately diluted culture broth by using Biotech Analyzer AS210 (Asahi Chemical Industry). The results of the above analysis are shown in Table 7.

As for the 2247Δgls glnA14 strain, further improvement in the yield was recognized compared with the 2247Δgls strain. These results demonstrated that, in addition to disappearance or reduction of the GLS activity, enhancement of the GS activity was effective for the production of L-glutamine.

TABLE 7

L-Glutamine production by GLS-deficient strain and GLS-deficient and GS-enhanced strain

| Strain | OD$_{620}$(X101) | Gln (g/L) | Glu (g/L) | Gln yield (%) |
|---|---|---|---|---|
| ATCC 14067 | 0.469 | 13.4 | 35.2 | 13.8 |
| 2247Δgls | 0.456 | 18.8 | 31.0 | 19.2 |
| 2247Δgls glnA14 | 0.436 | 24.4 | 26.0 | 24.9 |

Reference Example (1) Measurement of Glutaminase Activity of Known L-Glutamine Producing Bacteria and 2247Δgls glnA14

The strains AJ11576 and AJ11577 which were obtained as stains tolerant to a substance having vitamin P activity (Japanese Patent Laid-open No. 56-164792), AJ 11573 and AJ11574 which were obtained as stains tolerant to α-ketomalonic acid (Japanese Patent Laid-open No. 56-151495), AJ12418 and AJ12419 which were obtained as strains tolerant to a peptide containing glutamic acid (Japanese Patent Laid-open No. 2-186994) and so forth are known as L-glutamine producing bacteria. The GLS activity of these L-glutamine producing bacteria and 2247Δgls glnA14 strains obtained in Example 4 was measured by the method described in Example 1. The results are shown in Table 8. All of these known L-glutamine producing strains had significant GLS activity.

TABLE 8

GLS activity of known L-glutamine producing bacteria and 2247Δgls glnA14

| Strain | | GLS activity (U/mg) |
|---|---|---|
| Brevibacterium flavum | ATCC 14067 | 0.19 |
| Corynebacterium glutamicum | ATCC 13032 | 0.17 |
| Brevibacterium flavum | 2247Δgls glnA14 | 0.010 |
| Brevibacterium flavum | AJ11576 | 0.21 |
| Corynebacterium glutamicum | AJ11577 | 0.14 |
| Brevibacterium flavum | AJ11573 | 0.13 |
| Corynebacterium glutamicum | AJ11574 | 0.18 |
| Brevibacterium flavum | AJ12418 | 0.16 |
| Corynebacterium acetoacidophilum | AJ12419 | 0.20 |

While the invention has been described in detail with reference to preferred embodiments thereof, it will be apparent to one skilled in the art that various changes can be made, and equivalents employed, without departing from the scope of the invention. Each of the aforementioned documents, and including the foreign priority JP2002-342287, is incorporated by reference herein in its entirety.

What is claimed is:

1. An isolated coryneform bacterium having L-glutamine-producing ability, wherein said bacterium has been modified by disrupting or mutating a glutaminase gene on the chromosome so that the glutaminase activity of the bacterium is reduced to 0.1 U/mg of cellular protein or less, wherein said glutaminase gene encodes a protein comprising the amino acid sequence of SEQ ID NO: 2.

2. The bacterium of claim 1, wherein said glutaminase activity is ½ or less than glutamine synthetase activity when measured as activity per unit weight of cellular proteins.

3. The bacterium of claim 1, which is further modified by increasing the expression of a glutamine synthetase gene by increasing the copy number of said glutamine synthetase gene or by replacing a promoter region of said glutamine synthetase gene with a stronger promoter so that said glutamine synthetase activity of the bacterium is enhanced, wherein said glutamine synthetase gene is selected from the group consisting of:
   c) a DNA comprising the DNA sequence of SEQ ID NO: 3, and
   d) a DNA which is able to hybridize with the DNA of SEQ ID NO: 3 under stringent conditions of 1×SSC, 0.1% SDS, at 60° C., and is 95% or more homologous to SEQ ID NO: 3, and which encodes a protein which has glutamine synthetase activity.

4. The bacterium of claim 3, wherein said stronger promoter is selected from the group consisting of the lac promoter, trp promoter, and trc promoter.

5. The bacterium of claim 1, wherein the glutaminase activity of the bacterium is reduced to 0.01 U/mg of cellular protein or less.

6. The bacterium of claim 5, wherein said glutaminase activity is ½ or less than glutamine synthetase activity when measured as activity per unit weight of cellular proteins.

7. The bacterium of claim 5, which is further modified by increasing the expression of a glutamine synthetase gene by increasing the copy number of said glutamine synthetase gene or by replacing a promoter region of said glutamine synthetase gene with a stronger promoter so that said glutamine synthetase activity of the bacterium is enhanced, wherein said glutamine synthetase gene is selected from the group consisting of:
   c) a DNA comprising the DNA sequence of SEQ ID NO: 3, and
   d) a DNA which is able to hybridize with the DNA of SEQ ID NO: 3 under stringent conditions of 1×SSC, 0.1% SDS, at 60° C., and is 95% or more homologous to SEQ ID NO: 3, and which encodes a protein which has glutamine synthetase activity.

8. The bacterium of claim 7, wherein said stronger promoter is selected from the group consisting of the lac promoter, trp promoter, or trc promoter.

9. The bacterium of claim 1, wherein said glutaminase activity is reduced by disrupting a glutaminase gene on the chromosome.

10. The bacterium of claim 1, wherein said glutaminase activity is reduced by mutating a glutaminase gene on the chromosome.

* * * * *